US011950885B2

United States Patent
Wada et al.

(10) Patent No.: US 11,950,885 B2
(45) Date of Patent: Apr. 9, 2024

(54) BIOSENSOR DEVICE

(71) Applicant: MITSUBISHI ELECTRIC CORPORATION, Tokyo (JP)

(72) Inventors: Saki Wada, Tokyo (JP); Kengo Nishimoto, Tokyo (JP); Yasuhiro Nishioka, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 625 days.

(21) Appl. No.: 17/261,394

(22) PCT Filed: Aug. 7, 2019

(86) PCT No.: PCT/JP2019/031220
§ 371 (c)(1),
(2) Date: Jan. 19, 2021

(87) PCT Pub. No.: WO2020/039941
PCT Pub. Date: Feb. 27, 2020

(65) Prior Publication Data
US 2021/0259562 A1   Aug. 26, 2021

(30) Foreign Application Priority Data
Aug. 23, 2018   (WO) .................. PCT/JP2018/031085

(51) Int. Cl.
*A61B 5/0205*   (2006.01)
*A61B 5/024*   (2006.01)
*A61B 5/05*   (2021.01)

(52) U.S. Cl.
CPC ........ *A61B 5/0205* (2013.01); *A61B 5/02444* (2013.01); *A61B 5/05* (2013.01)

(58) Field of Classification Search
CPC ...... A61B 5/0205; A61B 5/02444; A61B 5/05
See application file for complete search history.

(56) References Cited

U.S. PATENT DOCUMENTS 6,239,404 B1   5/2001 Lea et al.
2013/0196610 A1   8/2013 Sanji et al.
(Continued)

FOREIGN PATENT DOCUMENTS

JP   61-135235 A   6/1986
JP   2002-508883 A   3/2002
(Continued)

OTHER PUBLICATIONS

Chioukh et al., "Monitoring Vital Signs Using Remote Harmonic Radar Concept", Proceedings of the 41st European Microwave Conference, Oct. 10-13, 2011, Manchester, UK, pp. 1269-1272.
(Continued)

*Primary Examiner* — Tammie K Marlen
(74) *Attorney, Agent, or Firm* — Birch, Stewart, Kolasch & Birch, LLP

(57) ABSTRACT

Provided is a biosensor device including: a signal generating unit for generating a continuous wave signal; an antenna for emitting the continuous wave signal as a radio wave; a variable matching circuit for performing impedance matching between the signal generating unit and the antenna; a detection circuit for outputting a detection signal on the basis of the continuous wave signal generated by the signal generating unit and a reflected signal of a radio wave incident on the antenna; and a control unit for controlling an element value of the variable matching circuit from the detection signal in a predetermined period corresponding to one cycle or more time in which heartbeat and respiration waveforms can be measured on the basis of the detection signal.

3 Claims, 12 Drawing Sheets

(56) References Cited

U.S. PATENT DOCUMENTS

| | | | |
|---|---|---|---|
| 2016/0242660 A1 | 8/2016 | Sato | |
| 2018/0042499 A1 | 2/2018 | Sato | |
| 2021/0290074 A1* | 9/2021 | Ertin | .................... A61B 5/1495 |
| 2022/0175254 A1* | 6/2022 | Hui | ......................... H04W 4/38 |
| 2022/0409081 A1* | 12/2022 | Visser | .................... H02N 2/181 |

FOREIGN PATENT DOCUMENTS

| | | |
|---|---|---|
| JP | 2009-301747 A | 12/2009 |
| JP | 2013-179556 A | 9/2013 |
| KR | 10-2011-0120553 A | 11/2011 |
| WO | WO 2015/056740 A1 | 4/2015 |
| WO | WO 2016/140367 A1 | 9/2016 |

OTHER PUBLICATIONS

International Search Report for PCT/JP2018/031085 dated Nov. 6, 2018.
International Search Report for PCT/JP2019/031220 dated Nov. 5, 2019.

\* cited by examiner

BIOSENSOR DEVICE

TECHNICAL FIELD

The present invention relates to a biosensor device for acquiring heartbeat and respiration waveforms in a non-contact manner using a radio wave.

BACKGROUND ART

In recent years, with a progress of ageing society with fewer children, traffic accidents caused by sudden physical changes or physical changes due to aging are increasing. In addition, with a decrease in working population, a load per driver in a transportation industry is excessive, resulting in frequent accidents caused by fatigue or drowsy driving. Against such a background, research on technology for estimating physical condition and health condition from biological information such as heartbeat and respiration waveforms has been actively performed, and development of a biosensor device capable of stably acquiring heartbeat and respiration waveforms has been expected. In addition, as for an in-vehicle device, a device that is in non-contact with an occupant and does not place an occupant under restraint is desirable, and therefore a biosensor device using a radio wave is promising.

A Doppler sensor is generally used as a sensor using a radio wave, but a high frequency wave is used, and therefore it is difficult to accurately acquire heartbeat and respiration waveforms due to a large influence of reflection from an ambient environment and external noise.

Miniaturization is required for use as an in-vehicle device, but when a small-sized antenna that is smaller than a wavelength is used, a resonance frequency of the antenna changes due to an influence of a human body, and sensor sensitivity deteriorates. Therefore, it is difficult to accurately acquire heartbeat and respiration waveforms.

In order to solve such a problem, Patent Literature 1 discloses a sensor for reducing a change in sensitivity by using input signals with a plurality of frequencies even when a resonance frequency changes due to an influence of a human body.

CITATION LIST

Patent Literature

Patent Literature 1: WO 2015-056740 A

SUMMARY OF INVENTION

Technical Problem

Since a heartbeat sensor device of Patent Literature 1 uses input waves with a plurality of frequencies, local waves at a mixer in a quadrature detection circuit of a device component also have a plurality of frequencies. Therefore, a large number of inter modulation (IM) components are generated due to nonlinearity of the mixer, and it is difficult to measure and detect heartbeat and respiration waveforms with high accuracy. In addition, in order to use a plurality of frequencies, it is necessary to complicate a configuration of a transmission circuit including a signal generating unit and a bandpass filter, resulting in a problem that cost increases.

The present invention has been achieved in order to solve the above-described problem, and an object of the present invention is to obtain a biosensor device adapted to a change in installation ambient environment and having high detection accuracy and a simple configuration, by adaptively controlling an input impedance of a biosensor antenna that changes depending on an installation ambient condition such as a human body and automatically performing matching of the input impedance.

Solution to Problem

The biosensor device according to the present invention includes: a signal generator to generate a continuous wave signal; an antenna to emit the continuous wave signal as a radio wave; a variable matching circuit for performing impedance matching between the signal generator and the antenna; a detection circuit to output a detection signal on the basis of the continuous wave signal and a reflected signal of a radio wave incident on the antenna; and control circuitry to control an element value of the variable matching circuit from the detection signal in a predetermined period corresponding to one cycle or more time in which heartbeat and respiration waveforms can be measured on the basis of the detection signal. The detection circuit includes: a first mixer to multiply the continuous wave signal by the reflected signal; a phase shifter to convert a phase of the continuous wave signal by 90 degrees; and a second mixer to multiply output of the phase shifter by the reflected signal. The control circuitry includes a complex number conversion coefficient having amplitude and phase information in advance. The detection signal includes an I signal output from the first mixer of the detection circuit and a Q signal output from the second mixer. When time average values of the respective two signals of I and Q in the detection signal in a predetermined period corresponding to one cycle or more time in which heartbeat and respiration waveforms can be measured are represented by VI and VQ, respectively, a heartbeat waveform signal Vr is represented by Vr=VI−jVQ, and when a reflection coefficient of the variable matching circuit and the antenna is represented by Γm, the conversion coefficient is calculated by Γm/Vr obtained by dividing the reflection coefficient Γm by the heartbeat waveform signal Vr.

Advantageous Effects of Invention

The present invention can obtain a biosensor device adapted to a change in installation ambient environment and having high detection accuracy and a simple configuration by adaptively controlling an input impedance of a biosensor antenna that changes depending on an installation ambient condition such as a human body and automatically performing matching of the input impedance.

DESCRIPTION OF EMBODIMENTS

Hereinafter, in order to describe the present invention in more detail, embodiments for performing the present invention will be described with reference to the attached drawings.

First Embodiment

Figure 1:
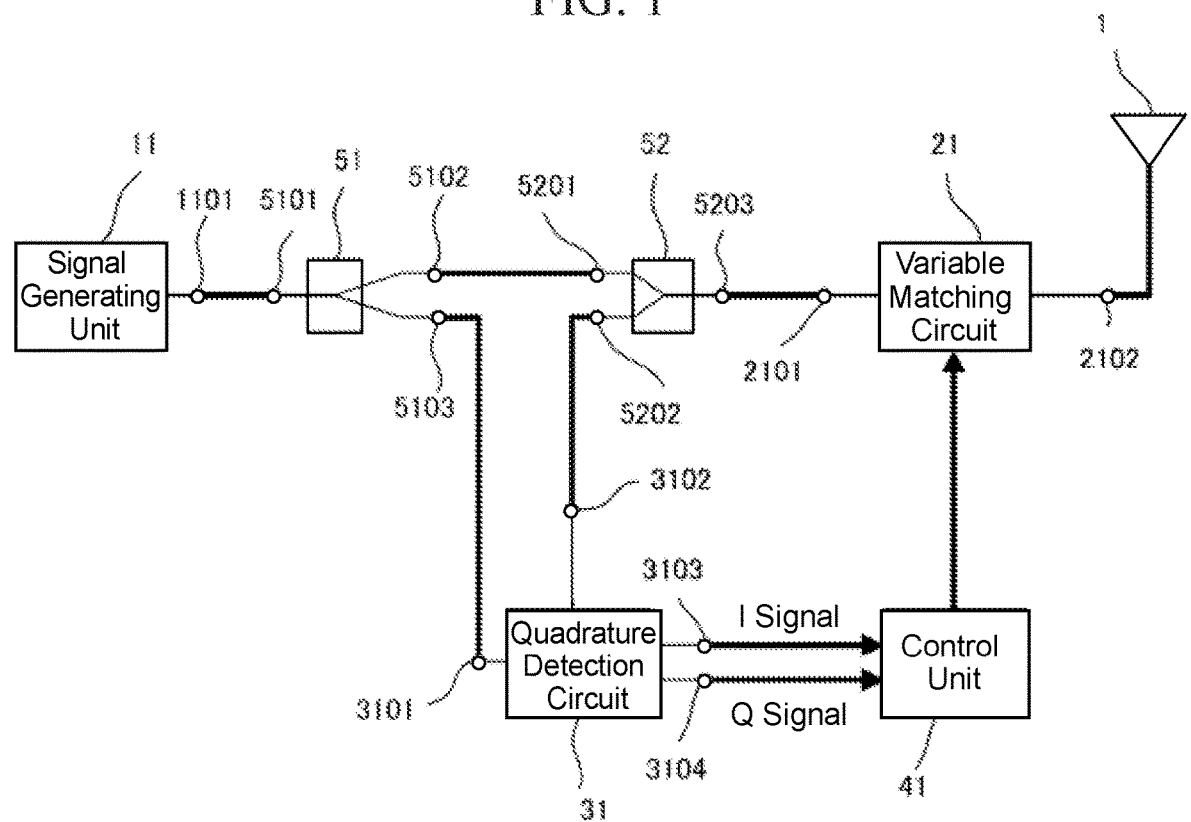
FIG. 1 is a configuration diagram illustrating a biosensor device according to a first embodiment.

FIG. 1 is a configuration diagram illustrating a biosensor device according to the present embodiment. In FIG. 1, the biosensor device according to the present embodiment includes an antenna 1, a signal generating unit 11, a variable matching circuit 21, a quadrature detection circuit 31, a control unit 41, and distribution circuits 51 and 52.

The antenna 1 is a small-sized antenna that is smaller than a wavelength and can be a loop antenna or a dipole antenna. The installation position of the antenna 1 is not limited in the present embodiment, and for example, by installing the antenna 1 near the heart of a measurement subject, it is possible to improve detection accuracy of heartbeat and respiration waveforms.

The signal generating unit 11 is a signal generator for generating a continuous wave of a frequency and has an output terminal 1101.

The variable matching circuit 21 has two terminals 2101 and 2102, matches a load impedance connected to the terminal 2102 (second and third terminals connected to the antenna 1) with an impedance of a circuit connected to the terminal 2101 (first terminal), and can change its passing and reflection characteristics.

Note that, in the present embodiment, a case where the variable matching circuit 21 includes three variable capacitance elements and one inductor will be described. An example of the variable matching circuit 21 is illustrated in FIG. 2.

Figure 2:
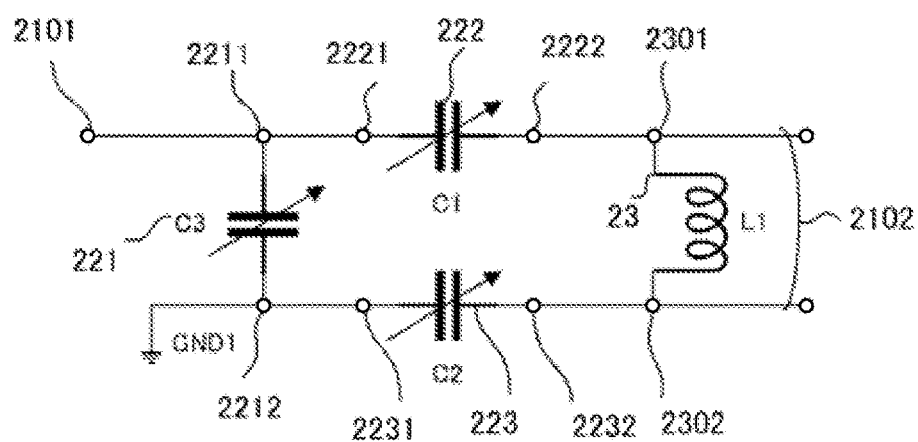
FIG. 2 is an example of a configuration diagram of a variable matching circuit 21 according to the first embodiment.

In FIG. 2, the reference numeral 221 represents a third variable capacitance element, the reference numeral 222 represents a first variable capacitance element, the reference numeral 223 represents a second variable capacitance element, and the reference numeral 23 represents an inductor element. Note that the variable capacitance element may be a variable capacitance diode.

The third variable capacitance element 221 has terminals 2211 and 2212, the first variable capacitance element 222 has terminals 2221 and 2222, the second variable capacitance element 223 has terminals 2231 and 2232, and the inductor element 23 has terminals 2301 and 2302. Note that the terminal 2212 is connected to the ground.

The terminal 2211 of the third variable capacitance element 221 and the terminal 2221 of the first variable capacitance element 222 are connected to each other, the terminal 2212 of the third variable capacitance element 221 and the terminal 2231 of the second variable capacitance element 223 are connected to each other, the terminal 2222 of the first variable capacitance element 222 and the terminal 2301 of the inductor element 23 are connected to each other, and the terminal 2232 of the second variable capacitance element 223 and the terminal 2302 of the inductor element 23 are connected to each other.

Next, operation of the variable matching circuit 21 will be described.

The variable matching circuit 21 controls values of the third variable capacitance element 221, the first variable capacitance element 222, and the second variable capacitance element 223 in accordance with a control signal transmitted from the control unit 41.

The quadrature detection circuit 31 has two input terminals (first input terminal 3101 and second input terminal 3102) and two output terminals (first output terminal 3103 and second output terminal 3104), subjects a signal input to the second input terminal 3102 to quadrature detection with a local signal input to the first input terminal 3101, outputs an in phase (I) signal from the output terminal 3103, and outputs a quadrature (Q) signal having a phase different from the I signal by 90 degrees to the output terminal 3104. An example of the quadrature detection circuit 31 is illustrated in FIG. 3.

Figure 3:
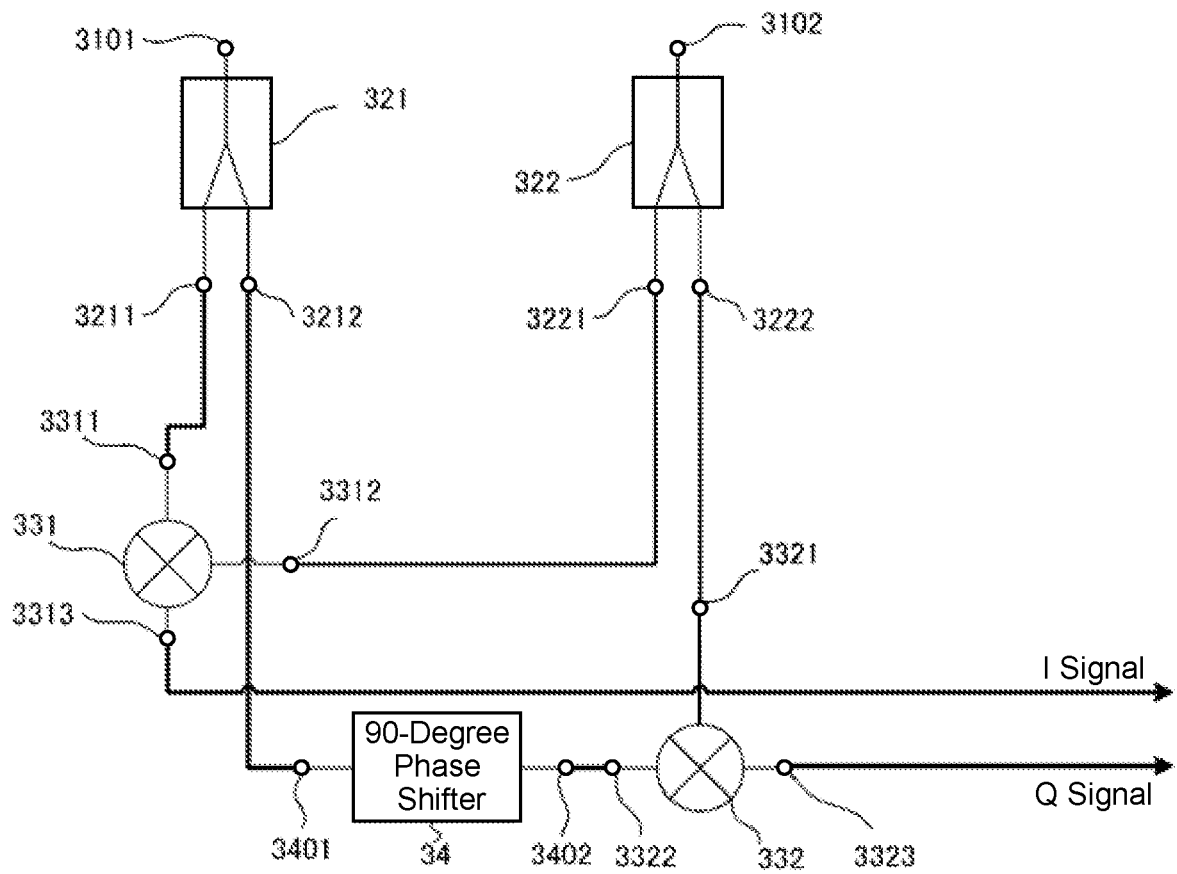
FIG. 3 is an example of a configuration diagram of a quadrature detection circuit 31 according to the first embodiment.

In FIG. 3, the reference numeral 321 represents a first distribution circuit, the reference numeral 322 represents a second distribution circuit, the reference numeral 331 represents a first mixer, the reference numeral 332 represents a second mixer, and the reference numeral 34 represents a 90-degree phase shifter (for shifting the phase of an input signal by 90 degrees).

The distribution circuit 321 is a high frequency circuit having three terminals 3101, 3211, and 3212, divides a signal input to the terminal 3101 into two signals, and outputs the signals to the terminals 3211 and 3212 as detection signals. Since the terminals 3211 and 3212 are isolated from each other, when a signal is input to the terminal 3211, no signal is output to the terminal 3212, and the signal is output only from the terminal 3101.

Similarly, the distribution circuit 322 is a high frequency circuit having three terminals 3102, 3221, and 3222, divides a signal input to the terminal 3102 into two signals, and outputs the signals to the terminals 3221 and 3222. Since the terminals 3221 and 3222 are isolated from each other, when a signal is input to the terminal 3221, no signal is output to the terminal 3222, and the signal is output only from the terminal 3102.

In the distribution circuits 321 and 322, output terminals only need to be isolated from each other, and therefore a Wilkinson type distributor or a directional coupler having an isolation terminal connected to a terminating resistor may be used.

The first mixer 331 has three terminals 3311, 3312, and 3313, multiplies signals input from the input terminals 3311 and 3312 by each other, and outputs the resulting signal from the output terminal 3313.

Similarly, the second mixer 332 has three terminals 3321 to 3323, multiplies signals input from the input terminals 3321 and 3322 by each other, and outputs the resulting signal from the output terminal 3323.

The 90-degree phase shifter 34 has two terminals 3401 and 3402, and outputs a signal obtained by shifting the phase of a signal input from the input terminal 3401 by 90 degrees, from the output terminal 3402.

As described above, a signal output from the terminal 3313 of the first mixer 331 and a signal output from the terminal 3323 of the second mixer 332 are output as an I signal and a Q signal, respectively.

The terminal 3211 of the first distribution circuit 321 and the terminal 3311 of the first mixer 331 are connected to each other, and the terminal 3221 of the second distribution circuit 322 and the terminal 3312 of the first mixer 331 are connected to each other.

The terminal 3212 of the first distribution circuit 321 and the terminal 3401 of the 90-degree phase shifter 34 are connected to each other, the terminal 3222 of the second distribution circuit 322 and the terminal 3321 of the second mixer are connected to each other, and the terminal 3402 of the 90-degree phase shifter 34 and the terminal 3322 of the second mixer are connected to each other.

Here, low pass filters (LPF) may be each installed between the terminal 3313 of the first mixer 331 and the control unit 41 and between the terminal 3323 of the second mixer and the control unit 41.

Next, operation of the quadrature detection circuit 31 will be described.

In the present embodiment, a signal input as a local signal from the terminal 3101 of the first distribution circuit 321 is divided into two signals for the terminals 3211 and 3212. A signal input, as a signal of a reflected wave reflected by a human body, from the terminal 3102 of the second distribution circuit 322 is divided into two signals for the terminals 3221 and 3222.

A signal output from the output terminal 3211 of the first distribution circuit 321 is input to the input terminal 3311 of the first mixer 331, and a signal output from the terminal 3221 of the second distribution circuit 322 is input to the input terminal 3312 of the first mixer 331.

The signal input to the input terminal 3311 and the signal input to the input terminal 3312 are multiplied by each other by the first mixer 331, and output from the output terminal 3313.

A signal output from the output terminal 3212 of the first distribution circuit 321 is input to the input terminal 3401 of the 90-degree phase shifter 34.

The 90-degree phase shifter 34 outputs a signal with a 90-degree phase shift to the output terminal 3402. The output signal is input to the input terminal 3322 of the second mixer 332.

A signal output from the output terminal 3222 of the second distribution circuit 322 is input to the mixer 332 from the terminal 3321 of the second mixer 332.

The mixer 332 multiplies the signals input from the input terminals 3321 and 3322 by each other, and outputs the resulting signal to the output terminal 3323.

As described above, a reflected signal coming from a human body, the signal being input to the terminal 3102 of the quadrature detection circuit 31, is subjected to quadrature detection by using a local signal input to the terminal 3101, and output from the terminals 3103 and 3104 of the quadrature detection circuit 31, as an I signal and a Q signal having phases different from each other by 90 degrees, respectively. The I signal and the Q signal are input to the control unit 41, as information such as amplitude.

The control unit 41 receives two waves of the I signal and the Q signal output from the quadrature detection circuit 31 as input, and records values of the I signal and the Q signal.

Furthermore, the control unit 41 calculates an average value of each of the I signals and the Q signals input during a predetermined fixed minute time (T), and outputs a control signal to the variable matching circuit 21 in such a manner that an absolute value of a time average value of each of the I signals and the Q signals is equal to or less than a small certain threshold.

The time (T) needs at least one cycle time in which heartbeat and respiration waveforms can be measured. Note that the heartbeat and respiration waveforms fluctuate largely depending on, for example, the sex, age, and mental state of a human body to be measured, and therefore it is desirable to use numerical values as large as possible.

Figure 4:
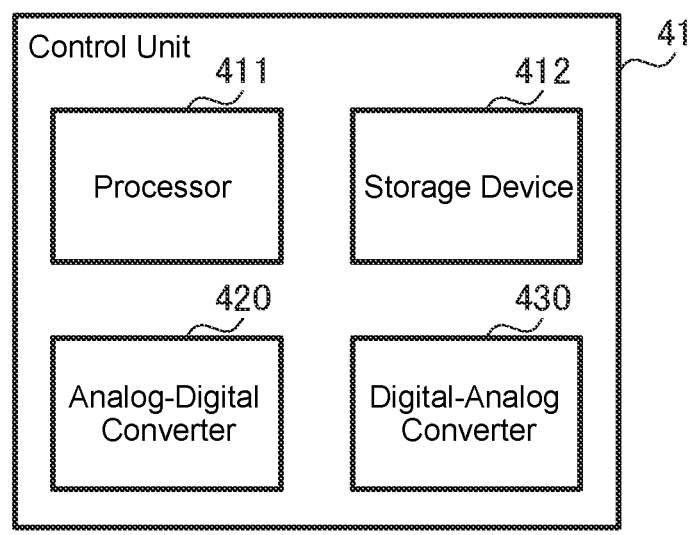
FIG. 4 is an example of a hardware configuration diagram of a control unit 41 according to the first embodiment.

FIG. 4 illustrates a block diagram schematically illustrating a specific example of a hardware configuration of the control unit 41.

As illustrated in FIG. 4, the control unit 41 includes: an analog-digital converter 420 for converting an I signal and a Q signal, which are analog signals output from the quadrature detection circuit 31, into digital signals; a storage device 412 for storing values of the I signal and the Q signal; a processor 411 for controlling the variable matching circuit from the I signal and the Q signal; and a digital-analog converter 430 for converting digital data into an analog signal.

The storage device 412 is a general term for a memory such as a read only memory (ROM) or random access memory (RAM), and an external storage device such as a hard disk, a program and data in the storage device 412 are read and written by the processor 411, and the storage device 412 is also used as a storage destination of temporary data. The storage device 412 is also used for reading and writing of the I signal and the Q signal output from the quadrature detection circuit 31 to the control unit 41. Furthermore, a program (control program) for performing matching of the variable matching circuit 21 is also stored in the storage device 412.

The analog-digital converter 420 converts an analog signal output from the quadrature detection circuit 31 into digital data that can be controlled by the processor 411.

The digital-analog converter 430 converts digital data resulting from arithmetic operation of the processor 411 into an analog signal that can be received by the variable matching circuit 21.

Note that the analog-digital converter 420 and the digital-analog converter 430 may use hardware for performing dedicated processing or a program for performing dedicated processing.

Operation of a control program executed by the processor 411 will be described by referring to FIG. 5.

Figure 5:
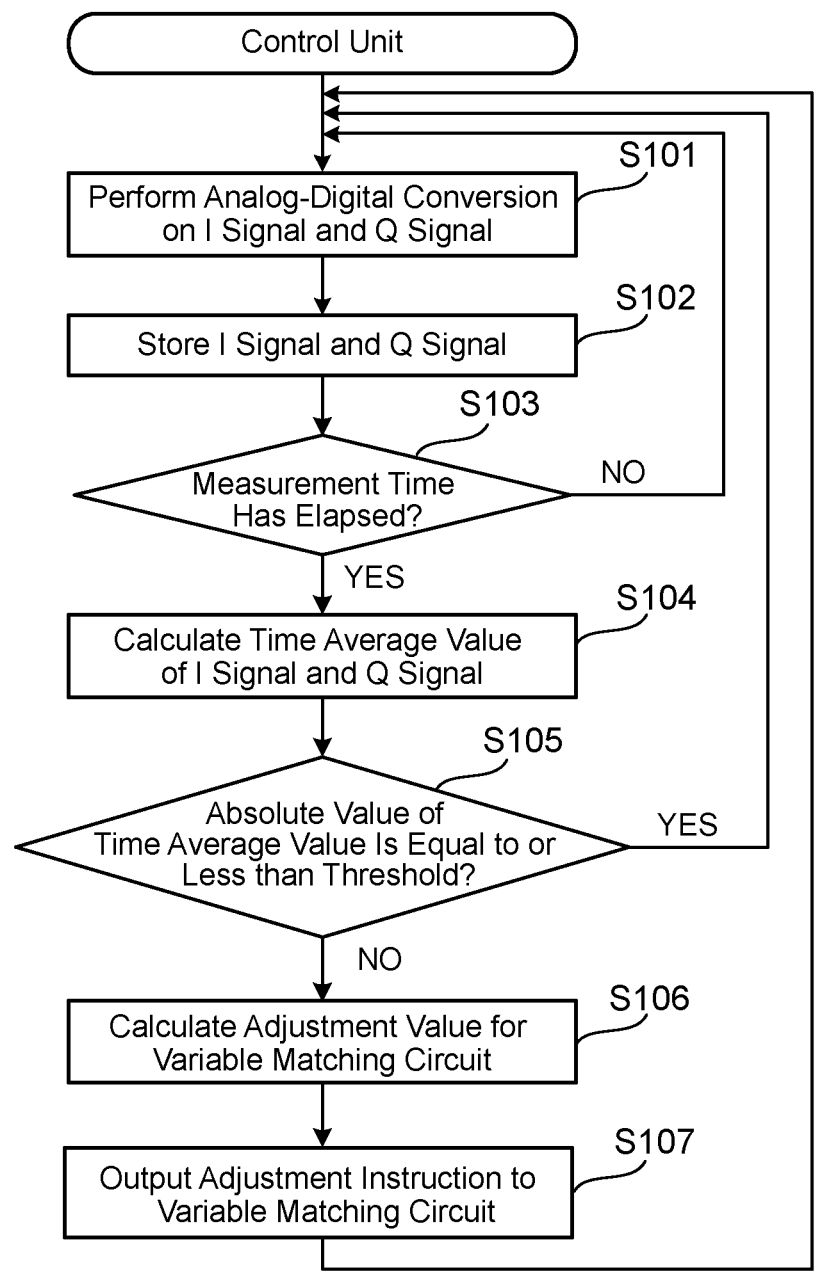
FIG. 5 is a flowchart for explaining operation of the control unit 41.

FIG. 5 is an example of a processing flow of a matching program operated by the control unit 41.

When the control program receives an I signal and a Q signal output from the quadrature detection circuit 31, the analog-digital converter 420 converts the I signal and the Q signal into digital signals (S101).

Next, the control program stores values of the I signal and the Q signal which have been converted into digital signals, in the storage device 412 (S102).

The control program determines whether a preset time (T) has elapsed (S103).

As a result, if the time (T) has not yet elapsed (S103:NO), the control program returns to the process of S101. If the time (T) has elapsed (S103: YES), the control program calculates an average value of each of the I signals and the Q signals stored in the storage device 412 during a period from the time going back by the time (T) to the current time (S104).

Next, the control program compares the average value with a preset threshold (S105). If the average value is less than the threshold (S105: YES), the control program returns to the process of S101. If the average value is equal to or more than the threshold (S105: NO), the control program calculates an adjustment value in such a manner that a load impedance connected to the terminal 2102 of the variable matching circuit 21 is matched with an impedance of a circuit connected to the terminal 2101 (S106).

Then, finally, the control program outputs the adjustment value to the variable matching circuit 21 (S107).

Thereafter, the control program repeats the process of S101 each time the control program receives the I signal and the Q signal output from the quadrature detection circuit 31 again.

Note that in the present embodiment, as a method for taking a time average, a certain measurement time is set to T seconds, and the entire time average of each of the I signals and the Q signals is taken. Alternatively, T seconds may be further divided into smaller sections, and waveforms may be weighed and averaged between the sections.

For example, when a time average up to S seconds (S≤T) in T seconds is represented by A(S), A(S) is averaged in a period of T−u≤S≤T (u≤T), and it is determined whether an absolute value of a time average value of each of the I signals and the Q signals is equal to or less than a sufficiently small certain threshold.

The threshold is determined by an influence of noise in an environment in which actual measurement is performed. For example, some numerical values of ambient noise may be measured, and a maximum value thereof may be used, or a proper value may be determined appropriately from a standard deviation value determined, or a maximum value and an average value or a most frequent value. The threshold may be set again without being fixed in such a manner that the threshold can be changed depending on a situation, for example, by measuring noise at regular intervals.

As a result, fluctuation of A(S) with respect to S is reduced, and therefore an error in taking an average value is reduced.

In order to calculate an adjustment value in such a manner that a load impedance connected to the terminal 2102 of the variable matching circuit 21 is matched with an impedance of a circuit connected to the terminal 2101, the following method can be considered.

First, a method for performing calculation from values of an I signal and a Q signal input to the control unit 41 and values of the variable capacitance elements 221 to 223 of the variable matching circuit 21 in such a manner that a Z characteristic impedance ($Z_0$) of the variable matching circuit 21 is 50Ω, and adjusting capacitances of the variable capacitance elements 221 to 223 in such a manner that an absolute value of a time average of each of the I signals and the Q signals falls below a threshold can be considered.

In addition, a capacitance value of each of the variable capacitance elements 221 to 223 may be adjusted, by sweeping the values of the variable capacitance elements 221 to 223 in such a manner that the absolute value of a time average of each of the I signals and the Q signals falls below the threshold.

For example, a value of the first variable capacitance element 222 is represented by C1, and a value of the second variable capacitance element 223 is represented by C2. Then, when the capacitance values of C1 and C2 satisfy a1≤C1≤a2 and b1≤C2≤b2, respectively, first, the value of C1 is fixed to a1, the value of C2 is gradually changed between b1 and b2, and it is determined whether a total time average value of each of the I signals and the Q signals falls below the threshold in the variable matching circuit in a state where the values of C1 and C2 are combined.

When the total time average value does not fall below the threshold even though all the values between b1 and b2 are used as C2, the value of C1 is changed, the value of C2 is changed from b1 to b2 again, and it is determined whether a total time average value of each of the I signals and the Q signals falls below the threshold in the variable matching circuit in a state where the values of C1 and C2 are combined.

Furthermore, a method of preparing a table storing proper values as capacitance values that can be taken by C1 and C2 in advance, from values of the I signals and the Q signals received by the control unit 41 and the average value of each of the values of the I signals and the Q signals, can be considered.

When receiving values of the I signal and the Q signal, the control unit 41 refers to this table, and can adjust a value of a variable element of the variable matching circuit 21 in a short time in such a manner that an absolute value of a time average of each of the I signals and the Q signals falls below the threshold, by using capacitance values to which C1 and C2 should be set, indicated by the table.

The distribution circuit 51 is a high frequency circuit having three terminals 5101 to 5103, and when a signal is input to the terminal 5101, the distribution circuit 51 divides the signal into two signals, and outputs the signals to the terminals 5102 and 5103.

Since the terminals 5102 and 5103 are isolated from each other, when a signal is input to the terminal 5102, no signal is output to the terminal 5103, and the signal is output only from the terminal 5101.

Similarly to the distribution circuit 51, the distribution circuit 52 is also a high frequency circuit having three terminals 5201 to 5203, and when a signal is input to the terminal 5203, the distribution circuit 51 divides the signal into two signals, and outputs the signals to the terminals 5202 and 5201.

Since the terminals 5202 and 5201 are isolated from each other, when a signal is input to the terminal 5201, no signal is output to the terminal 5202, and the signal is output only from the terminal 5203.

Note that in the distribution circuits 51 and 52, output terminals only need to be isolated from each other, and therefore a Wilkinson type distributor or a directional coupler having an isolation terminal connected to a terminating resistor may be used.

The output terminal 1101 of the signal generating unit 11 and the terminal 5101 of the first distribution circuit 51 are connected to each other, the terminal 5102 of the first distribution circuit 51 and the terminal 5201 of the second distribution circuit 52 are connected to each other, the terminal 5103 of the first distribution circuit 51 and the terminal 3101 of the quadrature detection circuit 31 are connected to each other, the terminal 5202 of the second distribution circuit 52 and the terminal 3102 of the quadrature detection circuit 31 are connected to each other, the terminal 5203 of the second distribution circuit 52 and the terminal 2101 of the variable matching circuit 21 are connected to each other, and the terminal 2102 of the variable matching circuit and the antenna 1 are connected to each other.

Next, overall operation of the biosensor device according to the present embodiment will be described. First, a signal of a frequency output from the output terminal 1101 of the signal generating unit 11 is input to the terminal 5101 of the first distribution circuit 51, and is divided into two signals for the terminals 5102 and 5103.

Here, a path a through which a signal passes is defined as a path of terminal 5102→terminal 5201→distribution circuit 52→terminal 5203→terminal 2101→variable matching circuit 21→terminal 2102.

A path b through which a signal passes is defined as a path of terminal 2102→variable matching circuit 21→terminal 2101→terminal 5203→distribution circuit 52→terminal 5202→terminal 3102.

A signal output from the terminal 5102 of the first distribution circuit 51 is input to the antenna 1 through the path a, and a signal output from the terminal 5103 of the first distribution circuit 51 is input from the terminal 3101 of the quadrature detection circuit 31 to the quadrature detection circuit 31, as a local signal.

A signal passing through the path a is emitted as a radio wave from the antenna 1, and a signal of a reflected wave reflected by a human body is input to the antenna 1 and input from the terminal 3102 of the quadrature detection circuit 31 to the quadrature detection circuit 31 through the path b.

The reflected signal coming from a human body, the signal being input to the terminal 3102 of the quadrature detection circuit 31, is subjected to quadrature detection by using a local signal input to the terminal 3101, and output from the terminals 3103 and 3104 of the quadrature detection circuit 31, as an I signal and a Q signal having phases different from each other by 90 degrees, respectively.

The I signal and the Q signal are input to the control unit 41.

The control unit 41 measures two waves of the input I signal and Q signal for a certain period of time, and calculates a time average of each of the I signals and the Q signals. It is determined whether an absolute value of the time average value of each of the I signals and the Q signals is equal to or less than a sufficiently small certain threshold.

When the absolute value of the time average value of each of the I signals and the Q signals is more than the threshold, the control unit 41 transmits a control signal to the variable matching circuit 21, and adjusts passage and reflection characteristics of the variable matching circuit 21 in such a manner that the absolute value of the time average of each of the I signals and the Q signals is equal to or less than the threshold.

As described above, as the absolute value of the time average value of each of the I signals and the Q signals determined by subjecting a signal of a radio wave emitted from the antenna and a signal of a reflected wave reflected by a human body to quadrature detection is sufficiently small and approaches 0, a mismatch loss of the impedance of the antenna is reduced, and sensor sensitivity can be improved.

In addition, by causing the control unit 41 to operate all the time while the biosensor device is operating, it is possible to perform measurement with high sensing sensitivity for a heartbeat all the time even when an installation ambient environment such as a human body changes.

Figure 6:
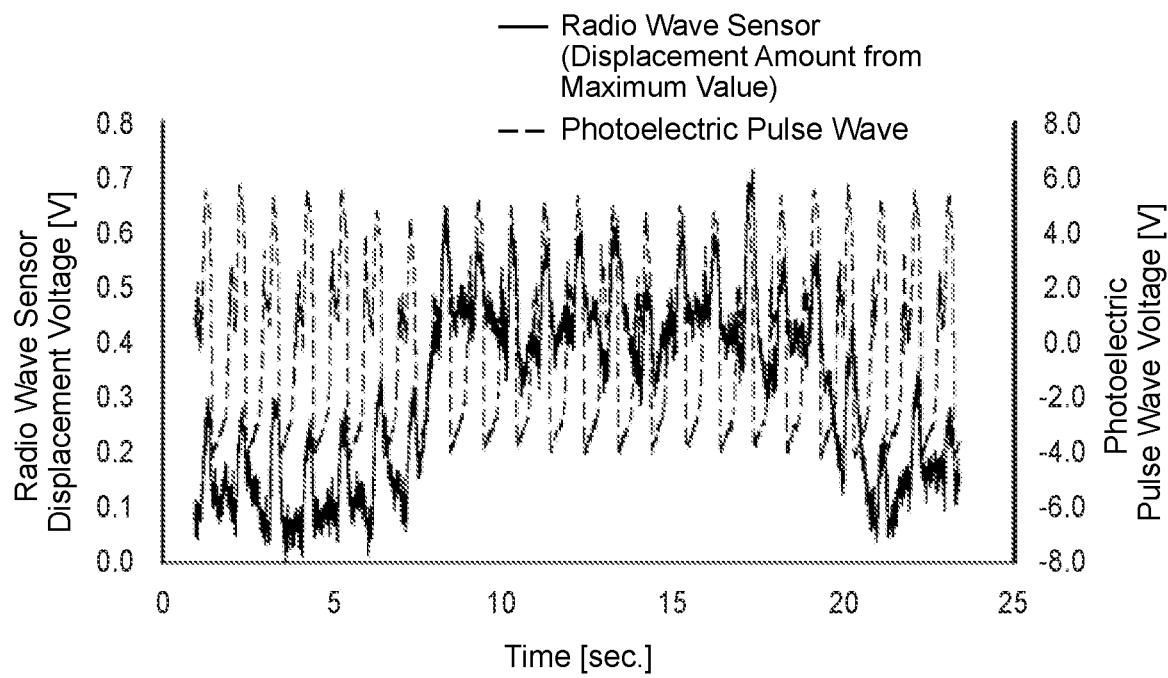
FIG. 6 is an example of heartbeat and respiration waveforms measured using the biosensor device according to the first embodiment.

FIG. 6 illustrates waveforms in a case where heartbeat and respiration waveforms of a measurement subject to whom measurement has been actually performed are acquired with the biosensor device used in the present embodiment.

Figure 7:
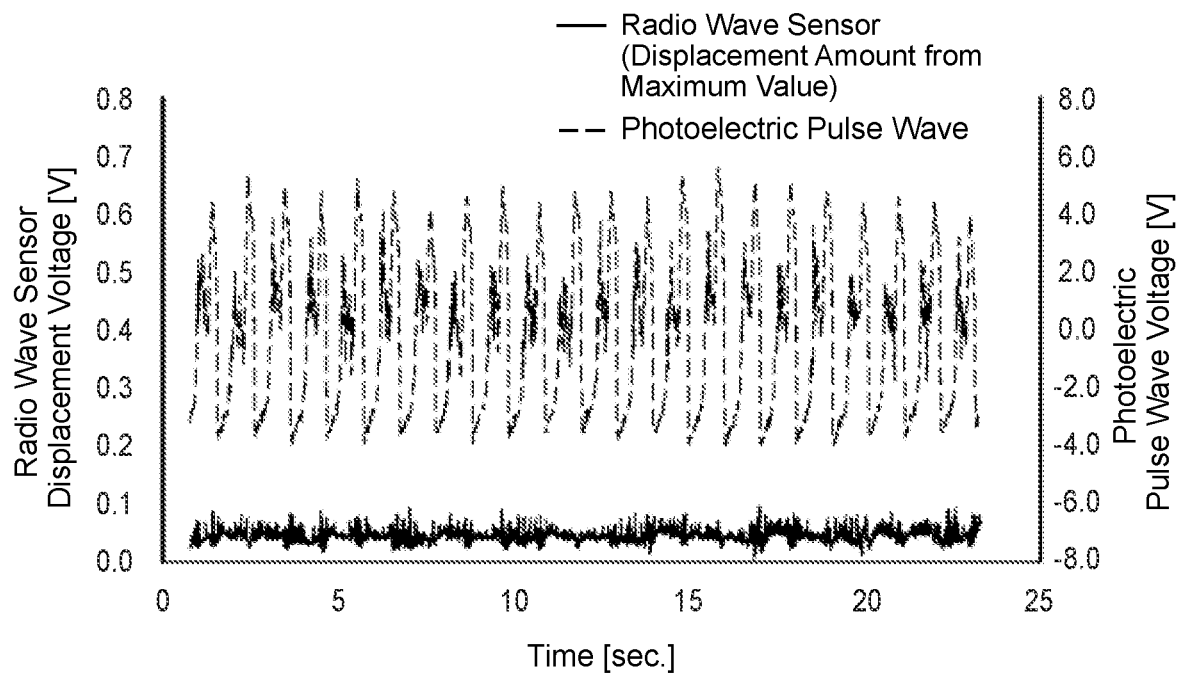
FIG. 7 is an example of heartbeat and respiration waveforms measured using a conventional biosensor device.

For comparison, FIG. 7 illustrates waveforms in a case where heartbeat and respiration waveforms are acquired using a biosensor device which does not include a variable matching circuit and whose antenna impedance is matched in free space. In both figures, results using a contact photoelectric pulse wave meter are displayed in wavy lines, as correct heartbeat and respiration waveforms (reference waveforms) of the measurement subject.

In both FIGS. 6 and 7, amplitudes of the obtained I signal and Q signal are calculated, and a displacement amount from a maximum value of each of the amplitudes is plotted.

FIG. 6 illustrates heartbeat and respiration waveforms obtained by using the biosensor device having the above-described configuration, and it can be confirmed that the positions of peaks thereof match those of the reference waveforms. Meanwhile, FIG. 7 illustrates heartbeat and respiration waveforms obtained by using a biosensor device not including a variable matching circuit, and it can be confirmed that the heartbeat and respiration waveforms of FIG. 7 have a smaller amplitude than those of FIG. 6, and behave in a different manner from the reference.

When peaks of the heartbeat waveform are accurately detected, a fluctuation value of a heartbeat interval of a measurement subject can be accurately measured, which can be widely applied to, for example, estimation of physical condition and health condition.

Note that in the present embodiment, the case has been described in which the control unit 41 makes a determination depending on whether the preset time (T) has elapsed, and when the time (T) has elapsed, an average value of each of the I signals and the Q signals stored in the storage device 412 is calculated during a period from the time going back by the time (T) to the current time. However, the control unit 41 may preset the number of times of receiving the values of the I signal and the Q signal without determining whether the time (T) has elapsed, and when the control unit 41 has received the values of each of the I signal and the Q signal by the number of times, an average value may be calculated from the values of each of the I signal and the Q signal for the preset number of times.

In addition, the result of whether or not the calculated average value of each of the I signals and the Q signals has exceeded the threshold may be stored each time, and the time (T) or the number of times may be changed depending on the result. For example, when the average value of each of the I signals and the Q signals has not exceeded the threshold, for example, three consecutive times, the time (T) or the number of times may be increased. Conversely, when the average value of each of the I signals and the Q signals has exceeded the threshold, for example, three consecutive times, the time (T) or the number of times may be decreased.

In this way, by increasing or decreasing the time (T) or the number of times, the operation of the control unit can be efficiently performed.

In the present embodiment, the case where the variable matching circuit 21 includes three variable capacitance elements and one inductor as illustrated in FIG. 2 has been described, but the configuration of the variable matching circuit 21 is not limited thereto.

The variable matching circuit 21 may have a configuration as illustrated in FIG. 8, 9, 10, 11, or 12.

Figure 8:
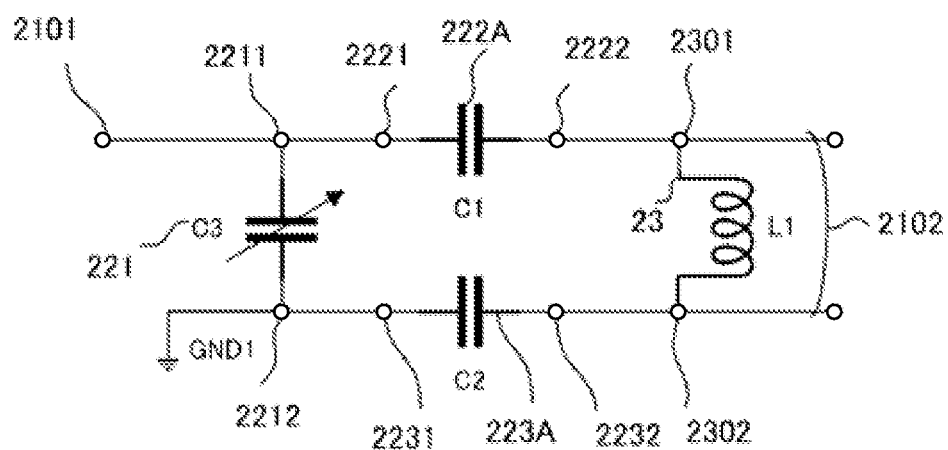
FIG. 8 is an example of the variable matching circuit 21 in a case where a first variable capacitance element 222 and a second variable capacitance element 223 are replaced with capacitor elements in the variable matching circuit 21 illustrated in FIG. 2.
Figure 9:
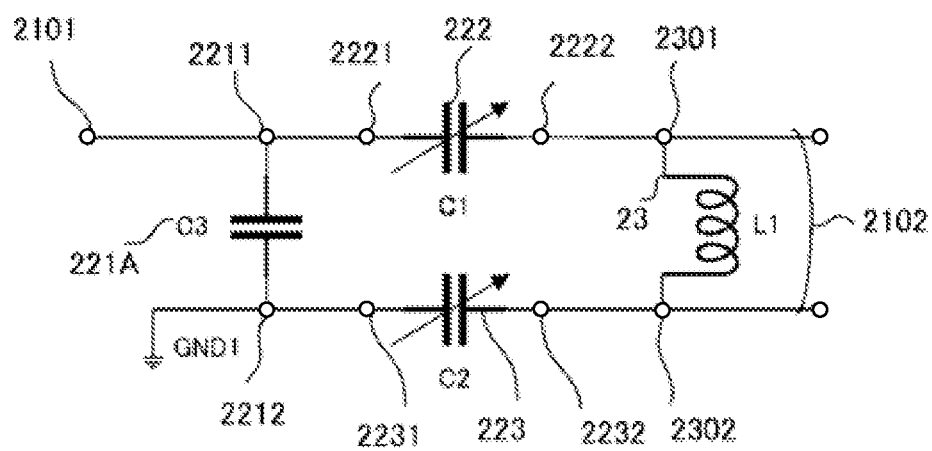
FIG. 9 is an example of the variable matching circuit 21 in a case where a third variable capacitance element 221 is replaced with a capacitor element in the variable matching circuit 21 illustrated in FIG. 2.

For example, the variable matching circuit 21 illustrated in FIG. 8 is obtained by replacing the first variable capacitance element 222 and the second variable capacitance element 223 of the variable matching circuit 21 illustrated in FIG. 2 with capacitor elements 222A and 223A having certain fixed values, respectively. The variable matching circuit 21 illustrated in FIG. 9 is obtained by replacing the third variable capacitance element 221 of FIG. 2 with a capacitor element 221A having a certain fixed value.

Figure 10:
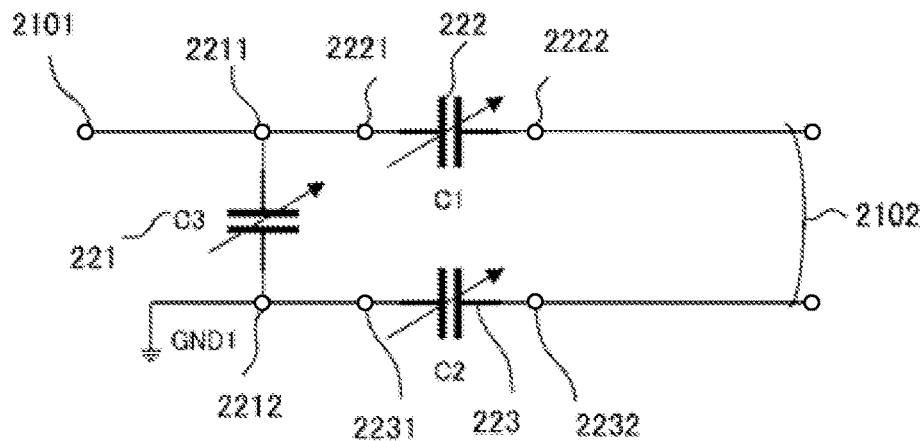
FIG. 10 is an example of the variable matching circuit 21 in a case where an inductor element is removed from the variable matching circuit 21 illustrated in FIG. 2.
Figure 11:
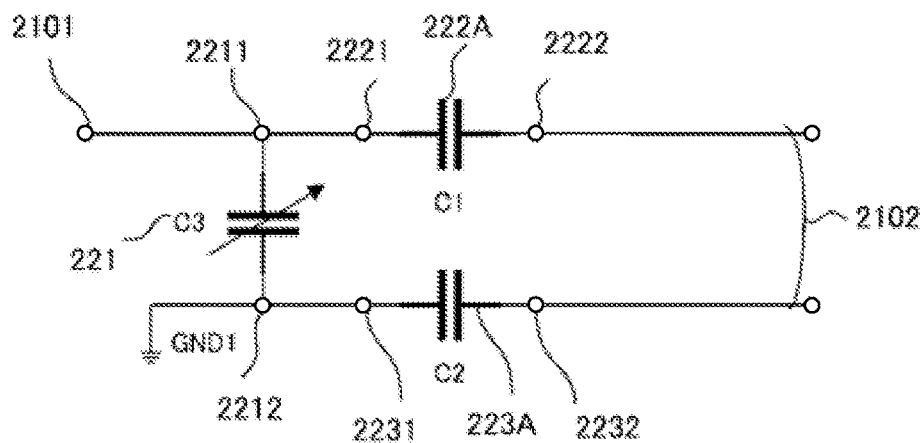
FIG. 11 is an example of the variable matching circuit 21 in a case where an inductor element is removed from the variable matching circuit 21 illustrated in FIG. 8.
Figure 12:
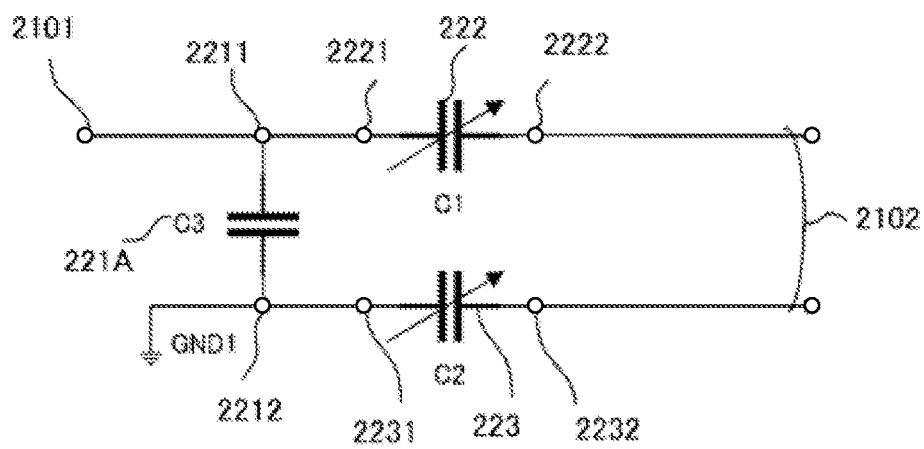
FIG. 12 is an example of the variable matching circuit 21 in a case where an inductor element is removed from the variable matching circuit 21 illustrated in FIG. 9.

The variable matching circuit 21 illustrated in FIG. 10 is obtained by removing the inductor element 23 from the variable matching circuit 21 illustrated in FIG. 2. The variable matching circuit 21 illustrated in FIG. 11 is obtained by removing the inductor element 23 from the variable matching circuit 21 illustrated in FIG. 8. The variable matching circuit 21 illustrated in FIG. 12 is obtained by removing the inductor element 23 from the variable matching circuit 21 illustrated in FIG. 9.

Furthermore, in FIGS. 8, 9, 10, 11, and 12, the third variable capacitance element 221 or the capacitor element 221A having a certain fixed value may be open. The first variable capacitance element 222 or the capacitor element 222A having a certain fixed value, and the second variable capacitance element 223 or the capacitor element 223A having a certain fixed value may be short-circuited. However, it is assumed that the first variable capacitance element and the second variable capacitance element have the same value and state.

As described above, by constituting the biosensor device by using the antenna 1, the signal generating unit 11, the variable matching circuit 21, the quadrature detection circuit 31, the control unit 41, and the distribution circuits 51 and 52, and controlling the variable matching circuit 21 by the control unit 41 in such a manner that an absolute value of a time average value of each of the I signals and the Q signals is equal to or less than a certain threshold, a biosensor device adapted to a change in installation ambient environment and having high detection accuracy and a simple configuration can be obtained.

Second Embodiment

Although the biosensor device using the distributor has been described in the first embodiment, a case of using a directional coupler instead of the distributor will be described in the present embodiment.

Figure 13:
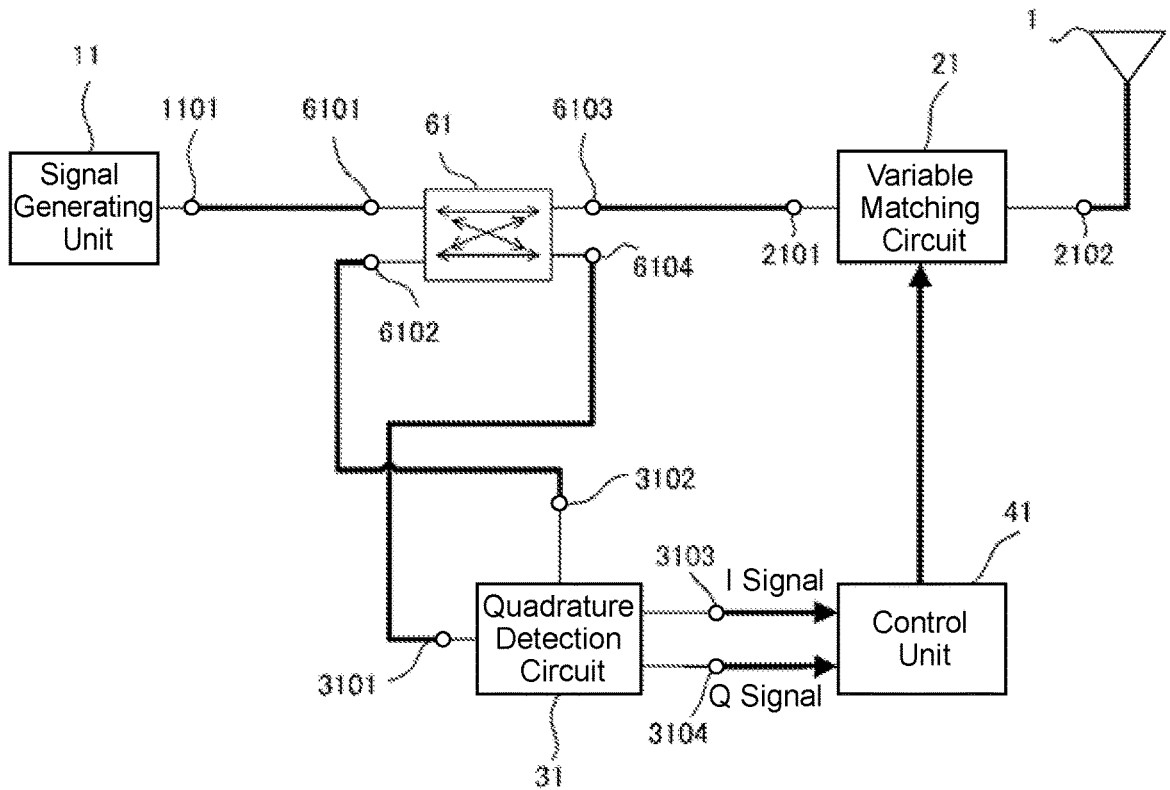
FIG. 13 is a configuration diagram illustrating a biosensor device according to a second embodiment.

FIG. 13 is a configuration diagram of the biosensor device according to the present embodiment.

In FIG. 13, the reference numeral 61 represents a directional coupler. In the present embodiment, a case where the directional coupler 61 has four terminals 6101 to 6104 will be described.

Note that in FIG. 13, the same reference numerals as in FIG. 1 indicate the same or corresponding parts.

When a signal is input to the terminal 6101, the directional coupler 61 divides the signal into two signals and outputs the signals to the terminals 6103 and 6104. When a signal is input to the terminal 6103, the directional coupler 61 divides the signal into two signals and outputs the signals to the terminals 6101 and 6102. The terminals 6101 and 6102 are isolated from each other, and the terminals 6103 and 6104 are isolated from each other.

In the present embodiment, as illustrated in FIG. 13, the output terminal 1101 of the signal generating unit 11 and the terminal 6101 of the directional coupler 61 are connected to each other, the terminal 6102 of the directional coupler 61 and the terminal 3102 of the quadrature detection circuit 31 are connected to each other, the terminal 6103 of the directional coupler and the terminal 2101 of the variable matching circuit 21 are connected to each other, and the terminal 6104 of the directional coupler and the terminal 3101 of the quadrature detection circuit 31 are connected to each other.

Operation in the present embodiment will be described.

A signal output from the output terminal 1101 of the signal generating unit 11 is input to the terminal 6101 of the directional coupler 61, and the signal is divided into two signals for the terminals 6103 and 6104.

A signal output from the terminal 6104 of the directional coupler 61 is input to the terminal 3101 of the quadrature detection circuit 31, as a local signal. A signal output from the terminal 6103 of the directional coupler 61 is input to the variable matching circuit 21 from the terminal 2101, output from the terminal 2102 to the antenna 1, and emitted from the antenna 1 as a radio wave.

The signal emitted from the antenna 1 is reflected by a human body and input to the antenna 1 as a reflected signal. The reflected signal is input to the terminal 2102 of the variable matching circuit 21, output from the terminal 2101, and input to the terminal 6103 of the directional coupler 61.

A part of the reflected signal input to the terminal 6103 is output from the terminal 6102 and input to the terminal 3102 of the quadrature detection circuit 31.

Similarly to the case of the first embodiment, a reflected signal coming from a human body, the signal being input to the terminal 3102 of the quadrature detection circuit 31, is subjected to quadrature detection by using a local signal input to the terminal 3101, and output from the terminals 3103 and 3104 of the quadrature detection circuit 31, as an I signal and a Q signal having phases different from each other by 90 degrees, respectively. The I signal and the Q signal are input to the control unit 41.

The control unit 41 measures two waves of the input I signal and Q signal for a certain period of time, and calculates a time average of each of the I signals and the Q signals. It is determined whether an absolute value of the time average value of each of the I signals and the Q signals is equal to or less than a sufficiently small certain threshold.

When the absolute value of the time average value of each of the I signals and the Q signals is more than the threshold, the control unit 41 transmits a control signal to the variable matching circuit 21, and adjusts passage and reflection characteristics of the variable matching circuit 21 in such a manner that the absolute value of the time average of each of the I signals and the Q signals is equal to or less than the threshold.

As described above, in the present embodiment, by constituting the biosensor device by using the antenna 1, the signal generating unit 11, the variable matching circuit 21, the quadrature detection circuit 31, the control unit 41, and the directional coupler 61, and controlling the variable matching circuit 21 by the control unit 41 in such a manner that an absolute value of a time average value of each of the I signals and the Q signals is equal to or less than a certain threshold, a biosensor device adapted to a change in installation ambient environment and having high detection accuracy and a simpler configuration can be obtained.

Third Embodiment

Although the biosensor device using the quadrature detection circuit has been described in the first embodiment, a case of using a mixer instead of the quadrature detection circuit will be described in the present embodiment.

Figure 14:
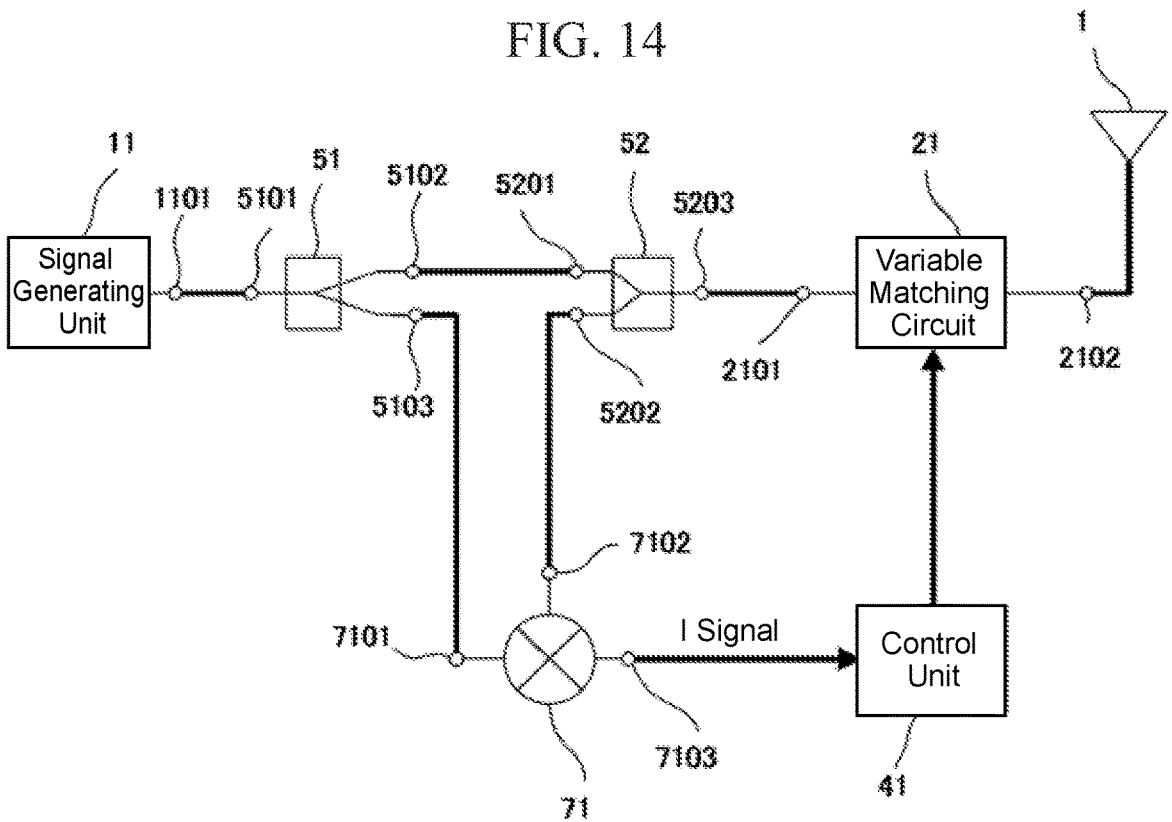
FIG. 14 is a configuration diagram illustrating a biosensor device according to a third embodiment.

FIG. 14 is a configuration diagram of the biosensor device according to the present embodiment.

In FIG. 14, the reference numeral 71 represents a mixer. In the present embodiment, a case where the mixer 71 has three terminals 7101 to 7103 will be described. Note that the reference numerals 7101 and 7102 represent input terminals, and the reference numeral 7103 represents an output terminal.

The mixer 71 multiplies signals input from the input terminals 7101 and 7102 by each other, and outputs the resulting signal from the output terminal 7103.

In the present embodiment, as illustrated in FIG. 14, the mixer 71 having the three terminals 7101 to 7103 is installed between the terminal 5103 of the first two-distribution circuit 51 and the terminal 5202 of the second two-distribution circuit 52.

Note that in FIG. 14, the same reference numerals as in FIG. 1 indicate the same or corresponding parts.

In the present embodiment, the terminal 5103 of the first two-distribution circuit 51 and the terminal 7101 of the mixer 71 are connected to each other, and the terminal 5202 of the second distribution circuit 52 and terminal 7102 of the mixer 71 are connected to each other. At this time, an LPF may be installed between the mixer 71 and the terminal 7103.

Operation in the present embodiment will be described.

A signal output from the output terminal 1101 of the signal generating unit 11 is input to the terminal 5101 of the first two-distribution circuit 51, and the signal is divided into two signals for the terminals 5102 and 5103.

Here, a path a through which a signal passes is defined as a path of terminal 5102→terminal 5201→two-distribution circuit 52→terminal 5203→terminal 2101→variable matching circuit 21→terminal 2102. A path b through which a signal passes is defined as a path of terminal 2102→variable matching circuit 21→terminal 2101→terminal 5203→two-distribution circuit 52→germinal 5202→terminal 7102.

A signal output from the terminal 5102 of the first two-distribution circuit 51 passes through the path a and is input to the antenna 1.

A signal output from the terminal 5103 of the first two-distribution circuit 51 is input from the terminal 7101 of the mixer 71 to the mixer 71, as a local signal.

A signal passing through the path a is emitted as a radio wave from the antenna 1. Then, a signal of a reflected wave reflected by a human body returns this time as an input to the antenna 1, passes through the path b, and is input to the mixer 71 from the terminal 7102 of the mixer 71.

A local signal input from the terminal 7101 of the mixer 71 and a reflected signal coming from a human body, the reflected signal being input from the terminal 7102, are multiplied by each other by the mixer 71, and output from the terminal 7103 of the mixer 71 as an I signal. This I signal is input to the control unit 41.

The control unit 41 measures the input I signal for a certain period of time, and calculates a time average of the I signals. It is determined whether an absolute value of the time average value of the I signals is equal to or less than a sufficiently small certain threshold. When the absolute value of the time average value of the I signals is more than the threshold, the control unit 41 transmits a control signal to the variable matching circuit 21, and adjusts passage and reflection characteristics of the variable matching circuit 21 in such a manner that the absolute value of the time average of the I signals is equal to or less than the threshold.

As described above, in the present embodiment, by constituting the biosensor device by using the antenna 1, the signal generating unit 11, the variable matching circuit 21, the control unit 41, the two two-distribution circuits 51 and 52, and the mixer 71, and controlling the variable matching circuit 21 by the control unit 41 in such a manner that the absolute value of the time average value of the I signals is equal to or less than a certain threshold, a biosensor device adapted to a change in installation ambient environment and having a simpler configuration can be obtained.

Fourth Embodiment

In the present embodiment, a case where a phase shifting circuit is further added will be described.

Figure 15:
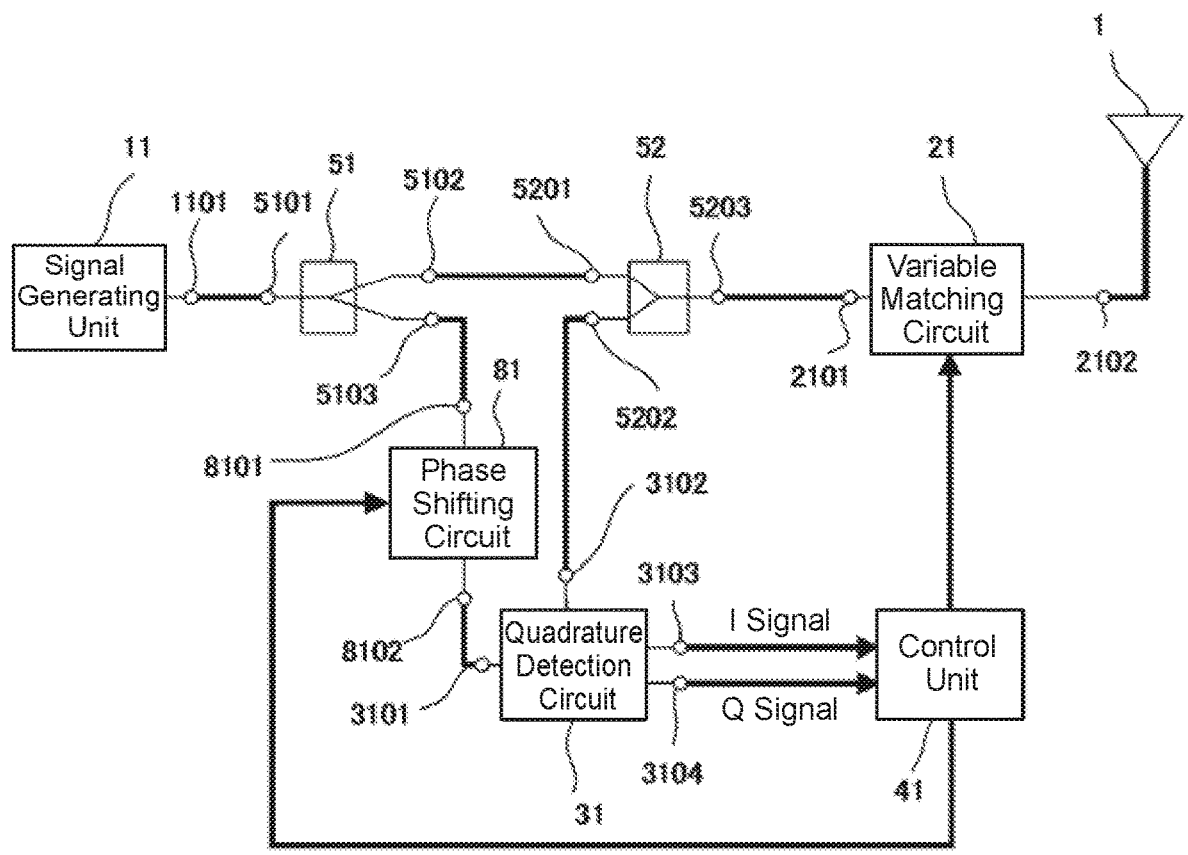
FIG. 15 is a configuration diagram illustrating a biosensor device according to a fourth embodiment.

FIG. 15 is a configuration diagram of a biosensor device according to the present embodiment.

In FIG. 15, the reference numeral 81 represents a phase shifting circuit. In the present embodiment, a case where the phase shifting circuit 81 has two terminals 8101 and 8102 will be described. Note that the reference numeral 8101 represents an input terminal, and the reference numeral 8102 represents an output terminal.

The phase shifting circuit 81 has a function of changing the phase of a local signal input from the input terminal 8101. The local signal whose phase has been changed by the phase shifting circuit 81 is output from the terminal 8102.

In the present embodiment, as illustrated in FIG. 15, the terminal 5103 of the first two-distribution circuit and the terminal 8101 of the phase shifting circuit 81 are connected to each other, and the terminal 8102 of the phase shifting circuit 81 and the terminal 3101 of the quadrature detection circuit 31 are connected to each other.

Note that in FIG. 15, the same reference numerals as in FIG. 1 indicate the same or corresponding parts.

Operation in the present embodiment will be described.

A signal output from the output terminal 1101 of the signal generating unit 11 is input to the terminal 5101 of the first two-distribution circuit 51, and divided into two signals for the terminals 5102 and 5103.

Here, a path a through which a signal passes is defined as a path of terminal 5102→terminal 5201→two-distribution circuit 452→terminal 5203→germinal 2101→variable matching circuit 21→terminal 2102. A path b through which a signal passes is defined as a path of terminal 2102→variable matching circuit 21→terminal 2101→terminal 5203→two-distribution circuit 52→terminal 5202→terminal 3102.

A signal output from the terminal 5102 of the first two-distribution circuit 51 is input to the antenna 1 through the path a, a signal output from the terminal 5103 of the first two-distribution circuit 51 is input as a local signal from the terminal 8101 of the phase shifting circuit 81 to the phase shifting circuit 81, output from the terminal 8102, and input from the terminal 3101 of the quadrature detection circuit 31 to the quadrature detection circuit 31.

A signal passing through the path a is emitted as a radio wave from the antenna 1, and a signal of a reflected wave reflected by a human body is input to the antenna 1 and input from the terminal 3102 of the quadrature detection circuit 31 to the quadrature detection circuit 31 through the path b.

The reflected signal coming from a human body, the signal being input to the terminal 3102 of the quadrature detection circuit 31, is subjected to quadrature detection by using a local signal input to the terminal 3101, and output from the terminals 3103 and 3104 of the quadrature detection circuit 31, as an I signal and a Q signal having phases different from each other by 90 degrees, respectively. The I signal and the Q signal are input to the control unit 41.

The control unit 41 measures two waves of the input I signal and Q signal for a certain period of time, and calculates a time average of each of the I signals and the Q signals. It is determined whether an absolute value of the time average value of each of the I signals and the Q signals is equal to or less than a sufficiently small certain threshold. When the absolute value of the time average value of each of the I signals and the Q signals is more than the threshold, the control unit 41 transmits a control signal to the variable matching circuit 21, and adjusts passage and reflection characteristics of the variable matching circuit 21 in such a manner that the absolute value of the time average of each of the I signals and the Q signals is equal to or less than the threshold.

Furthermore, the control unit 41 adjusts the amount of phase shift of the phase shifting circuit 81 in such a manner that a difference between a maximum value and a minimum value of the I signals within a certain period of time is a maximum.

In this way, by adjusting the amount of phase shift of the phase shifting circuit 81 in such a manner that a difference between a maximum value and a minimum value of the I signals within a certain period of time is a maximum, the amplitude of a heartbeat waveform can be maximized, and an SN ratio can be improved.

As described above, in the fourth embodiment, by constituting the biosensor device by using the antenna 1, the signal generating unit 11, the variable matching circuit 21, the quadrature detection circuit 31, the control unit 41, the two two-distribution circuits 51 and 52, and the phase shifting circuit 81, and adjusting the amount of phase shift of the phase shifting circuit 81 by the control unit 41 in such a manner that a difference between a maximum value and a minimum value of the I signals within a certain period of time is a maximum, a biosensor device having a maximized amplitude of a heartbeat waveform, an improved SN ratio, high detection accuracy, and a simple configuration can be obtained.

Fifth Embodiment

In the present embodiment, a case where an amplification circuit is further added will be described.

Figure 16:
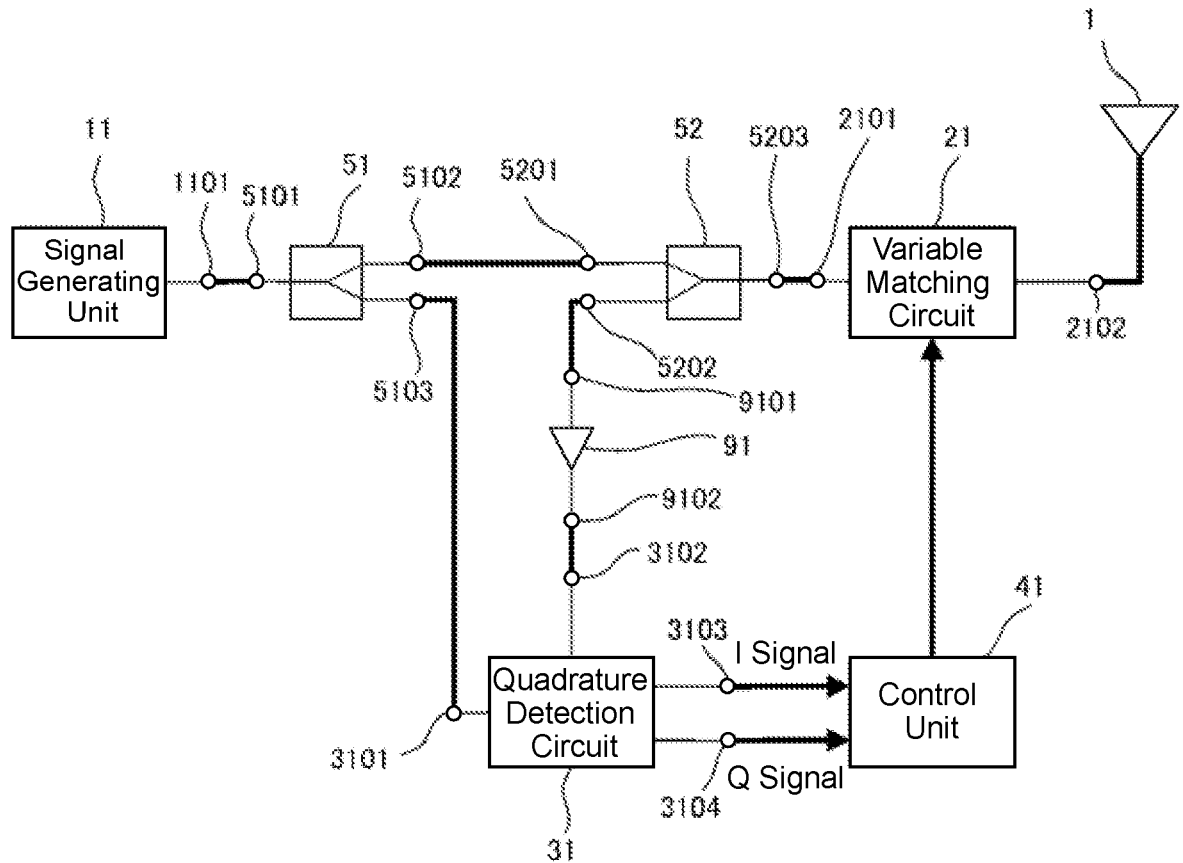
FIG. 16 is a configuration diagram illustrating a biosensor device according to a fifth embodiment.

FIG. 16 is a configuration diagram of a biosensor device according to the present embodiment.

In FIG. 16, the reference numeral 91 represents an amplification circuit. The amplification circuit 91 used in the present embodiment has two terminals 9101 and 9102, amplifies a signal input to the terminal 9101, and outputs the amplified signal from the terminal 9102.

In the present embodiment, as illustrated in FIG. 16, the terminal 5202 of the second two-distribution circuit 52 and the terminal 9101 of the amplification circuit 91 are connected to each other, and the terminal 9102 of the amplification circuit 91 and the terminal 3102 of the quadrature detection circuit 31 are connected to each other.

Note that in FIG. 16, the same reference numerals as in FIG. 1 indicate the same or corresponding parts.

Operation in the present embodiment will be described.

A signal output from the output terminal 1101 of the signal generating unit 11 is input to the terminal 5101 of the first two-distribution circuit 51, and the signal is divided into two signals for the two terminals 5102 and 5103.

Here, a path a through which a signal passes is defined as a path of terminal 5102→terminal 5201→two-distribution circuit 52→terminal 5203→terminal 2101→variable matching circuit 21→terminal 2102. A path b through which a signal passes is defined as a path of terminal 2102→variable matching circuit 21→terminal 2101→terminal 5203→two-distribution circuit 52→terminal 5202→terminal 9101.

A signal output from the terminal 5102 of the first two-distribution circuit 51 is input to the antenna 1 through the path a, and a signal output from the terminal 5103 of the first two-distribution circuit 51 is input as a local signal from the terminal 3101 of the quadrature detection circuit 31 to the quadrature detection circuit 31.

A signal passing through the path a is emitted as a radio wave from the antenna 1, a signal of a reflected wave reflected by a human body is input to the antenna 1 and input from the input terminal 9101 of the amplification circuit 91 to the amplification circuit 91 through the path b, and an amplified signal is output from the output terminal 9102 and input from the terminal 3102 of the quadrature detection circuit 31 to the quadrature detection circuit 31.

The reflected signal coming from a human body, the signal being input to the terminal 3102 of the quadrature detection circuit 31 and amplified by the amplification circuit 91, is subjected to quadrature detection by using a local signal input to the terminal 3101, and output from the terminals 3103 and 3104 of the quadrature detection circuit 31, as an I signal and a Q signal having phases different from each other by 90 degrees, respectively. The I signal and the Q signal are input to the control unit 41.

In this way, by amplifying a signal of a reflected wave coming from a human body by the amplification circuit 91, an SN ratio can be improved.

As described above, in the fifth embodiment, by constituting the biosensor device by using the antenna 1, the signal generating unit 11, the variable matching circuit 21, the quadrature detection circuit 31, the control unit 41, the two two-distribution circuits 51 and 52, and the amplification circuit 91, and amplifying a signal of a reflected wave coming from a human body by the amplification circuit 91, a biosensor device having an improved SN ratio, high detection accuracy, and a simple configuration can be obtained.

Sixth Embodiment

In the present embodiment, a case where the control unit 41 includes a conversion coefficient in the first embodiment will be described.

Figure 17:
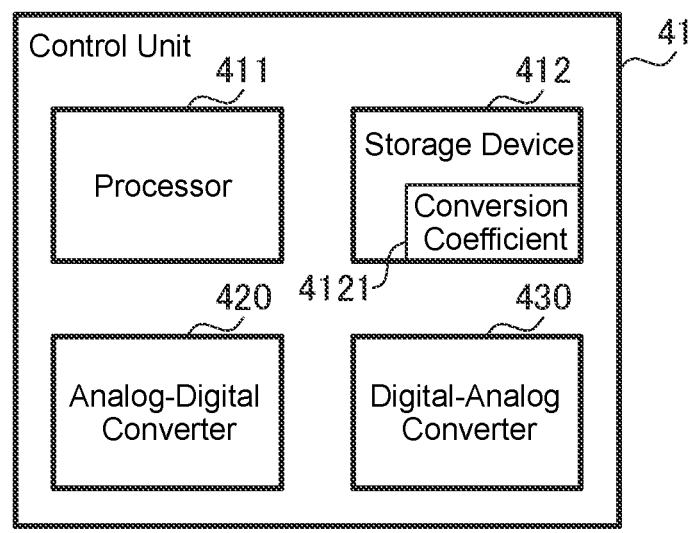
FIG. 17 is an example of a hardware configuration according to a sixth embodiment, which is a case where the hardware configuration illustrated in FIG. 4 includes a conversion coefficient.

FIG. 17 is a block diagram schematically illustrating a hardware configuration of the control unit 41, and illustrates a case where the storage device 412 of FIG. 4 in the first embodiment includes a conversion coefficient 4121.

The conversion coefficient 4121 is a coefficient stored in advance in the storage device 412, and has amplitude and phase information depending on the circuit configuration of FIG. 1. In addition, the conversion coefficient 4121 converts a time average value of each of the I signals and the Q signals into a reflection coefficient Γm of the antenna as viewed from the terminal 2101 of the variable matching circuit 21. The conversion coefficient may be determined and stored in the storage device 412 in advance, for example, before shipment of the biosensor device.

When the circuit configuration of FIG. 1 is changed, it is necessary to reset the conversion coefficient 4121. For example, when the variable matching circuit 21 and the distribution circuit 52 are connected to each other with a coaxial cable and the cable length changes, the conversion coefficient 4121 is reset.

A method for determining the conversion coefficient 4121 will be described. The conversion coefficient 4121 is determined, not in an environment in which the antenna 1 is installed near the heart or the like, but in an environment in which there is nothing moving around the antenna 1 and thus the I signal and the Q signal hardly fluctuate with time.

Using the circuit configuration of FIG. 1, the reflection coefficient Γm of the antenna as viewed from the terminal 2101 of the variable matching circuit 21, the reflection coefficient Γm of the antenna being obtained by changing the set value of the variable matching circuit 21, is measured with a vector network analyzer (VNA) or the like, an I signal and a Q signal at the same set value are measured in a similar manner, and values corresponding to each other are recorded.

Here, when voltages corresponding to the I signal and the Q signal are represented by VI and VQ, respectively, and a heartbeat waveform signal Vr satisfies Vr=VI−jVQ, the conversion coefficient 4121 can be calculated from formula (1).

$$Ae^{j\theta} = \Gamma_m / V_r \quad (1)$$

For the heartbeat waveform signal Vr corresponding to the reflection coefficient Γm, for example, a value obtained by calculating an amplitude term and a phase term from formula (1) using two points where VSWR is about 2 to 5 and which are separated from each other as much as possible, and by averaging the amplitude term and the phase term, is used as the conversion coefficient 4121. When VSWR is too large, the distribution circuit 52 deviates from ideal characteristic, and an error is large. When VSWR is small, measurement errors of VI, VQ, and S11 are large. Therefore, a value of VSWR used for the calculation is desirably about 2 to 5.

The conversion coefficient 4121 may be calculated for each set value of the variable matching circuit 21 using the heartbeat waveform signal Vr corresponding to the reflection coefficient Γm, or may be determined by calculating an amplitude term and a phase term for each set value of the variable matching circuit 21 using the heartbeat waveform signal Vr corresponding to the reflection coefficient Γm, and by averaging the values for all the points.

The storage device 412 includes the conversion coefficient 4121 determined from formula (1) in advance. Therefore, even in an environment having only the configuration of FIG. 1 and no other special measuring device, by multiplying the I signal and the Q signal which are detection signals of a heartbeat waveform, by the conversion coefficient 4121 (=$Ae^{j\theta}$), the reflection coefficient Γm of the antenna as viewed from the corresponding terminal 2101 of the variable matching circuit 21 can be determined.

Operation of a control program executed by the processor 411 in FIG. 17 will be described by referring to FIG. 18.

Figure 18:
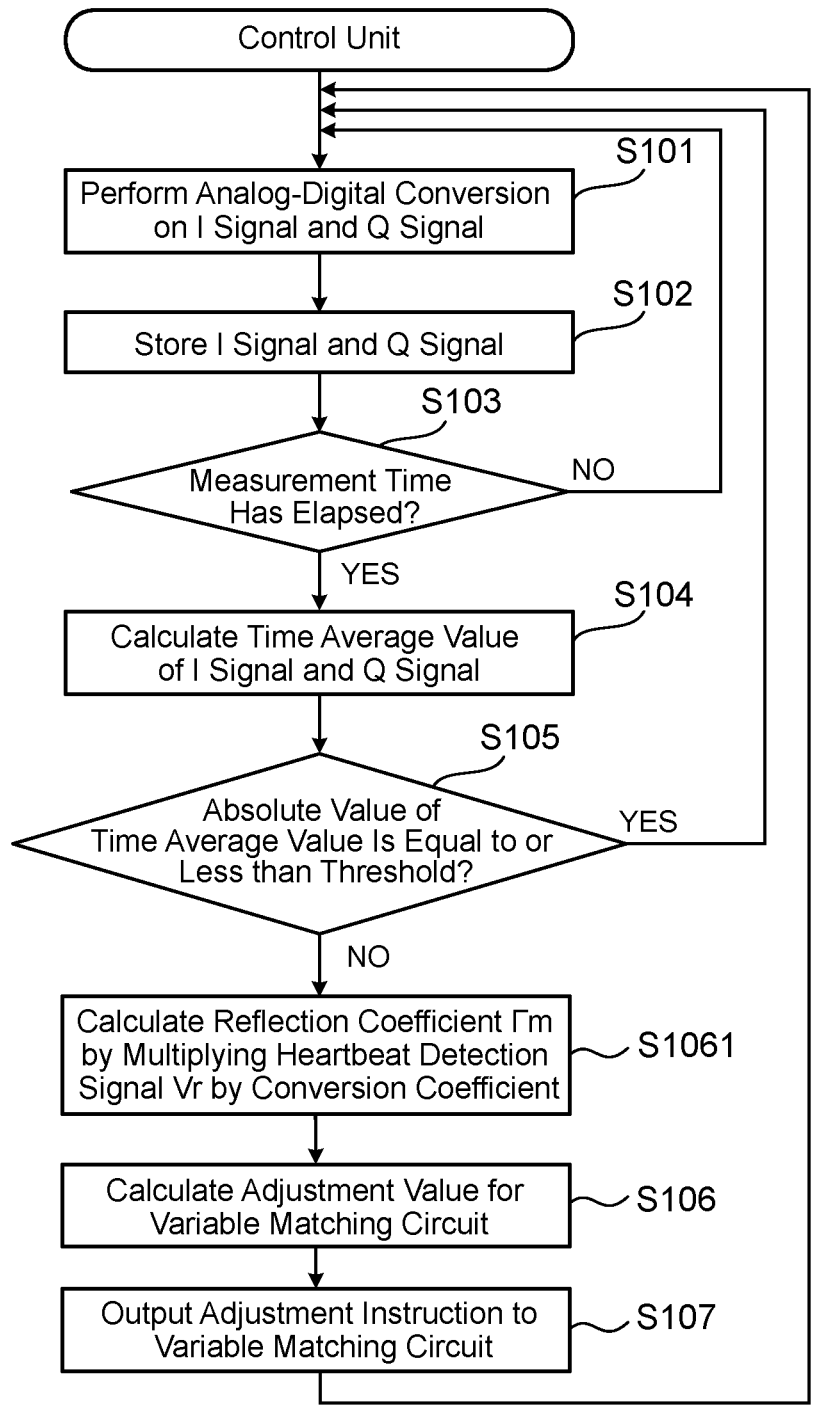
FIG. 18 is a flowchart for explaining operation of a control unit 41 according to the sixth embodiment.

FIG. 18 is an example of a processing flow of a matching program operated by the control unit 41.

When the control program receives an I signal and a Q signal output from the quadrature detection circuit 31, the analog-digital converter 420 converts the I signal and the Q signal into digital signals (S101).

Next, the control program stores values of the I signal and the Q signal which have been converted into digital signals in the storage device 412 (S102).

The control program determines whether a preset time (T) has elapsed (S103).

As a result, if the time (T) has not yet elapsed (S103: NO), the control program returns to the process of S101. If the time (T) has elapsed (S103: YES), the control program calculates an average value of each of the I signals and the Q signals stored in the storage device 412 during a period from the time going back by the time (T) to the current time (S104).

Next, the control program compares this average value with a preset threshold (S105). If the average value is less than the threshold (S105: YES), the control program returns to the process of S101. If the average value is equal to or more than the threshold (S105: NO), the control program calculates the reflection coefficient Γm of the antenna 1 as viewed from the terminal 2101 of the variable matching circuit 21 by multiplying the I signal and the Q signal stored in the storage device 412 by the conversion coefficient 4121 (=$Ae^{j\theta}$)° (S1061). Using the calculated reflection coefficient Γm, an adjustment value for the variable matching circuit 21 is calculated in such a manner that an impedance on the antenna 1 side as viewed from the terminal 2101 of the variable matching circuit 21 is an impedance (50Ω) of a circuit connected to the terminal 2101 (S106).

Then, finally, the control program outputs the adjustment value to the variable matching circuit 21 (S107).

By introducing the conversion coefficient 4121, even in an environment having only the configuration of FIG. 1 and no other special measuring device, the reflection coefficient Γm of the antenna as viewed from the terminal 2101 of the variable matching circuit 21 can be determined from a detection signal of the quadrature detection circuit 31. Therefore, an adjustment value for the variable matching circuit 21 can be accurately set, and a biosensor device having high detection accuracy and a simple configuration can be obtained.

Seventh Embodiment

In the present embodiment, a case where the control unit 41 adjusts the variable matching circuit 21 will be described using an example of the variable matching circuit 21 in the sixth embodiment.

Figure 19:
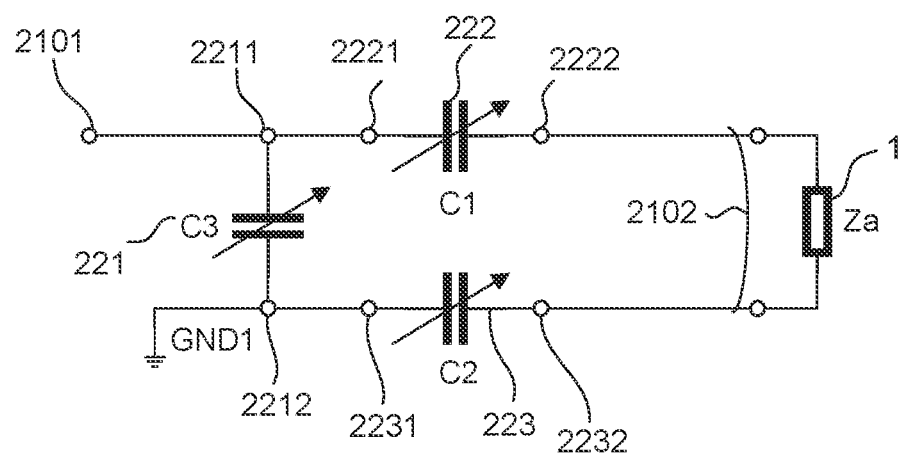
FIG. 19 is an example of the variable matching circuit 21 in a case where an antenna 1 having an antenna impedance of Za is connected in the variable matching circuit 21 illustrated in FIG. 10.
Figure 20:
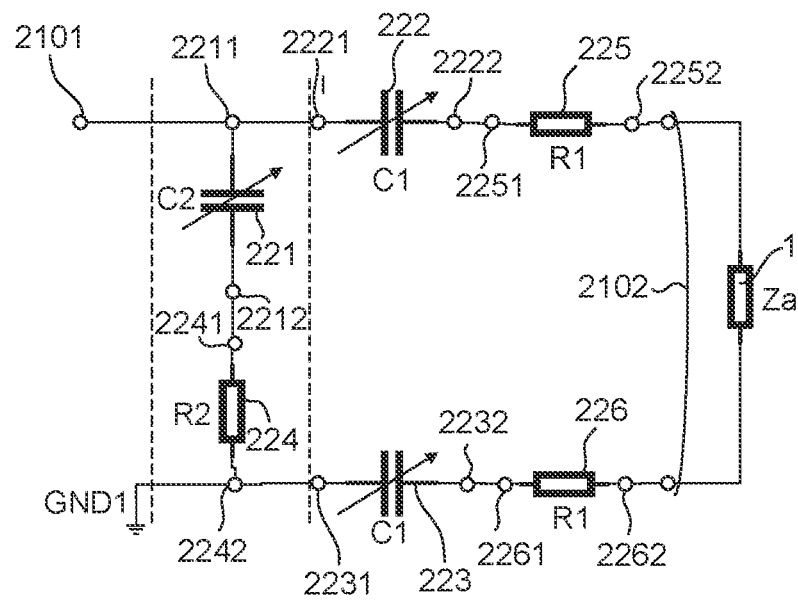
FIG. 20 is an example of an equivalent circuit of the variable matching circuit 21 illustrated in FIG. 19.

FIG. 19 illustrates a configuration of the variable matching circuit 21 described in the present embodiment, and FIG. 20 illustrates an equivalent circuit of FIG. 19.

Figure 21:
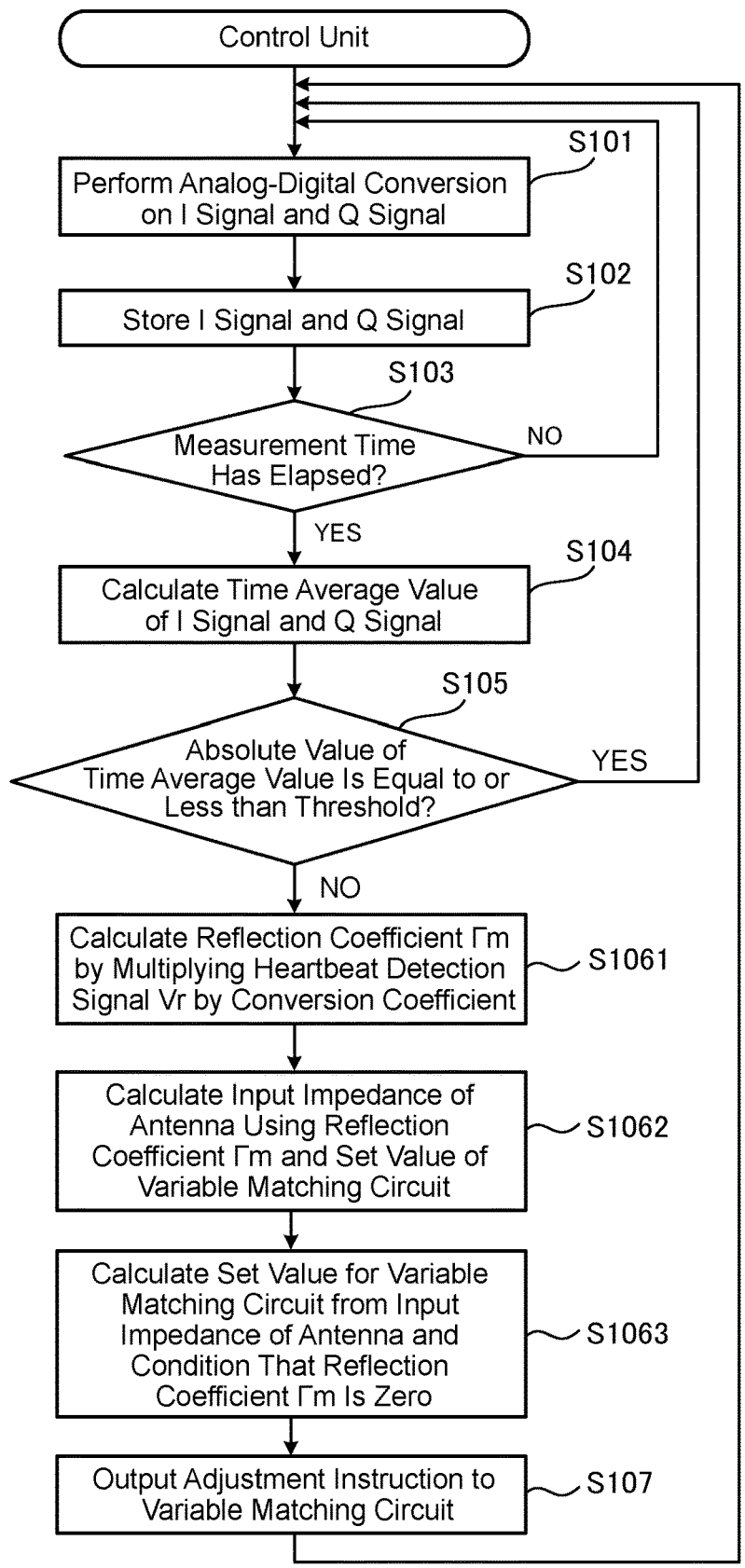
FIG. 21 is a flowchart for explaining operation of a control unit 41 according to a seventh embodiment.

FIG. 21 illustrates an example of a control flow described in the present embodiment.

FIG. 19 illustrates a configuration in which the terminals 2222 and 2232 of the first and second variable capacitance elements are connected to the terminal 2102 of the antenna 1 in FIG. 10 of the first embodiment. The antenna 1 connected to the terminal 2102 is illustrated as a load impedance Za of the antenna 1.

FIG. 20 illustrates an equivalent circuit of FIG. 19. When the circuit illustrated in FIG. 19 is formed, as illustrated in FIG. 20, actually, a parasitic resistance exists in each of the first, second, and third variable capacitance elements 222, 223, and 221. Therefore, it is necessary to consider the parasitic resistance when values of the first, second, and third variable capacitance elements 222, 223, and 221 are accurately calculated. Here, it is considered that the parasitic resistance is connected in series to each of the first, second, and third variable capacitance elements 222, 223, and 221.

The reference numeral 224 represents a third parasitic resistance connected to the third variable capacitance element 221, the reference numeral 225 represents a first parasitic resistance connected to the first variable capacitance element 222, and the reference numeral 226 represents a second parasitic resistance connected to the second variable capacitance element 223.

The third parasitic resistance 224 has terminals 2241 and 2242, the first parasitic resistance 225 has terminals 2251 and 2252, and the second parasitic resistance 226 has terminals 2261 and 2262. Note that the terminal 2242 is connected to the ground.

The terminal 2241 of the third parasitic resistance 224 and the terminal 2212 of the third variable capacitance element 221 are connected to each other, the terminal 2242 of the third parasitic resistance 224 and the terminal 2231 of the second variable capacitance element 223 are connected to each other, the terminal 2251 of the first parasitic resistance 225 and the terminal 2222 of the first variable capacitance element 222 are connected to each other, the terminal 2261 of the second parasitic resistance 226 and the terminal 2232 of the second variable capacitance element 223 are connected to each other, and the terminal 2252 of the first parasitic resistance 225 and the terminal 2262 of the second parasitic resistance 226 are connected to the terminal 2102 of the antenna 1. Note that a variable capacitance value of each of the first variable capacitance element 222 and the second variable capacitance element 223 is represented by C1, a variable capacitance value of the third variable capacitance element 221 is represented by C2, a resistance value of each of the first parasitic resistance 225 and the second parasitic resistance 226 is represented by R1, and a resistance value of the third parasitic resistance 224 is represented by R2.

In the present embodiment, operation of a control program executed by the processor 411 of FIG. 17 will be described by referring to FIG. 21.

When the control program receives an I signal and a Q signal output from the quadrature detection circuit 31, the analog-digital converter 420 converts the I signal and the Q signal into digital signals (S101).

Next, the control program stores values of the I signal and the Q signal which have been converted into digital signals in the storage device 412 (S102).

The control program determines whether a preset time (T) has elapsed (S103).

As a result, if the time (T) has not yet elapsed (S103: NO), the control program returns to the process of S101. If the time (T) has elapsed (S103: YES), the control program calculates an average value of each of the I signals and the Q signals stored in the storage device 412 during a period from the time going back by the time (T) to the current time (S104).

Next, the control program compares the average value with a preset threshold (S105). If the average value is less than the threshold (S105: YES), the control program returns to the process of S101. If the average value is equal to or more than the threshold (S105: NO), the control program calculates an adjustment value for the variable matching circuit unit 21 (S1061 to S1063). Then, finally, the control program outputs the adjustment value to the variable matching circuit 21 (S107).

Calculation of an adjustment value for the variable matching circuit unit 21 of the control program (S1061 to S1063) will be specifically described by referring to FIG. 20 which is an equivalent circuit of FIG. 19.

First, calculation in a subroutine S1061 of the control program will be described.

When time average values of the I signals and the Q signals stored in the storage device 412 are represented by VI and VQ, respectively, and a heartbeat waveform signal Vr satisfies Vr=VI−jVQ, by multiplying the heartbeat waveform signal Vr by the conversion coefficient 4121 (=$Ae^{j\theta}$), the reflection coefficient Γm of the antenna 1 as viewed from a reference plane t1 of the variable matching circuit 21 is calculated.

$$\Gamma_m = Ae^{j\theta} \cdot V_r \qquad (2)$$

Subsequently, calculation in a subroutine S1062 will be described.

An impedance Z=R+jX of the antenna 1 as viewed from the reference plane t1 of the variable matching circuit 21 is calculated from the reflection coefficient Γm calculated in S1061, and an impedance Za=Ra+jXa of the antenna connected to the terminal 2102 is calculated using the impedance Z, a current circuit constant of the variable matching circuit 21, and a frequency ω of a signal generated from the signal generating unit 11.

Specific calculation in S1062 is performed by solving simultaneous equations for the impedance of the antenna 1 as viewed from the reference plane t1 and a reference plane t2 illustrated in FIG. 20.

A real part and an imaginary part of the impedance Za=Ra+jXa of the antenna 1 are given by formulas (3) and (4), respectively.

$$R_a = \frac{R(1 + \omega^2 C_2^2 R_2^2 + 2\omega C_2 X) + \omega^2 C_2^2 R_2 (R^2 - X^2)}{(1 + \omega C_2 X)^2 + \omega^2 C_2^2 (R_2 + R)^2} - 2R_1 \qquad (3)$$

$$X_a = \frac{X(1 + \omega^2 C_2^2 R_2^2 + 2\omega C_2 R) - \omega C_2 (R^2 - X^2)}{(1 + \omega C_2 X)^2 + \omega^2 C_2^2 (R_2 + R)^2} + \frac{2}{\omega C_1} \qquad (4)$$

Subsequently, calculation in a subroutine S1063 will be described.

Capacitance values of the variable matching circuit 21 are calculated from the impedance Za of the antenna 1 determined in the subroutine S1062 and a condition that the reflection coefficient Γm of the antenna 1 as viewed from the reference plane t1 is zero (Z=R0=50Ω), and formulas (5) and (6) represent the respective capacitance values.

$$C_1 = \frac{2}{\omega \left( X_a - \dfrac{\omega C_2 R_0^2}{1 + \omega^2 C_2^2 (R_0 - R_2)^2} \right)} \qquad (5)$$

$$C_2 = \frac{1}{\omega} \sqrt{\frac{R_0 - (2R_1 + R_a)}{(R_2 - R_0)\{(R_2 - R_0)(R_a + 2R_1) - R_2 R_0\}}} \qquad (6)$$

Γm can be reduced by adjusting the variable capacitance values C1 and C2 using formulas (5) and (6).

Then, finally, the control program outputs the adjustment value to the variable matching circuit 21 (S107).

For example, when the variable capacitance element is a variable capacitance diode, for the adjustment value, the control unit 41 may include a table of the variable capacitance diode and applied voltage values corresponding to capacitance values of the variable capacitance diode, and from the calculated capacitance value, may indicate an applied voltage value which is the adjustment value to the variable matching circuit 21 in accordance with the information of the table.

By the calculation of the adjustment value for the variable matching circuit unit 21 (S1061 to S1063), the adjustment value for the variable matching circuit 21 can be set accurately, and a biosensor device having high detection accuracy and a simple configuration can be obtained.

Note that in the present invention, free combination of the embodiments, modification to any constituent element in each of the embodiments, or omission of any constituent element in each of the embodiments within the scope of the invention.

INDUSTRIAL APPLICABILITY

The biosensor device according to the present invention includes: a signal generating unit for generating a continuous wave signal; an antenna for emitting the continuous wave signal as a radio wave; a variable matching circuit for performing impedance matching between the signal generating unit and the antenna; a detection circuit for outputting a detection signal on the basis of the continuous wave signal and a reflected signal of a radio wave incident on the antenna; and a control unit for controlling an element value of the variable matching circuit from the detection signal in a predetermined period corresponding to one cycle or more time in which heartbeat and respiration waveforms can be measured on the basis of the detection signal, can adaptively control an input impedance of a biosensor antenna that changes depending on an installation ambient condition such as a human body, and is suitable for a biosensor device for acquiring heartbeat and respiration waveforms in a non-contact manner using a radio wave.

REFERENCE SIGNS LIST

1: Antenna, 11: Signal generating unit, 21: Variable matching circuit, 23: Inductor element, 31: Quadrature detection circuit, 34: 90-Degree phase shifter, 41: Control unit, 51: Distribution circuit, 52: Distribution circuit, 61: Directional coupler, 71: Mixer, 81: Phase shifting circuit, 91: Amplification circuit, 221: Third variable capacitance element, 221A: Capacitor element having a certain fixed value, 222: First variable capacitance element, 222A: Capacitor element having a certain fixed value, 223: Second variable capacitance element, 223A: Capacitor element having a certain fixed value, 224: Third parasitic resistance, 225: First parasitic resistance, 226: Second parasitic resistance, 321: First distribution circuit, 322: Second distribution circuit, 331: First mixer, 332: Second mixer, 411: Processor, 412: Storage device, 420: Analog-digital converter, 430: Digital-analog converter

The invention claimed is:

1. A biosensor device comprising:
a signal generator to generate a continuous wave signal;
an antenna to emit the continuous wave signal as a radio wave;
a variable matching circuit to perform impedance matching between the signal generator and the antenna;
a detection circuit to output a detection signal on a basis of the continuous wave signal and a reflected signal of the radio wave, reflected by a human body, and incident on the antenna; and
control circuitry to control a capacitance value of a capacitance element in the variable matching circuit from the detection signal in a predetermined period corresponding to one cycle or more time in which heartbeat and respiration waveforms can be measured on a basis of the detection signal,
wherein the detection circuit includes:
a first mixer to multiply the continuous wave signal by the reflected signal;
a phase shifter to convert a phase of the continuous wave signal by 90 degrees; and
a second mixer to multiply output of the phase shifter by the reflected signal, and wherein the control circuitry stores, in advance, a complex number conversion coefficient having amplitude and phase information,
the detection signal includes an I signal output from the first mixer of the detection circuit and a Q signal output from the second mixer, and
when time average values of the respective two signals of I and Q in the detection signal in a predetermined period corresponding to one cycle or more time in which heartbeat and respiration waveforms can be measured are represented by VI and VQ, respectively, a heartbeat waveform signal Vr is represented by Vr=VI−jVQ, and
when a reflection coefficient of the variable matching circuit and the antenna is represented by Γm,
the conversion coefficient is calculated by Γm/Vr obtained by dividing the reflection coefficient Γm by the heartbeat waveform signal Vr.

2. The biosensor device according to claim 1, wherein
the control circuitry adjusts a current circuit constant of the variable matching circuit by using an impedance of the antenna so as to reduce the reflection coefficient of the variable matching circuit and the antenna,
the load impedance of the antenna is calculated by using the reflection coefficient Γm of the variable matching circuit and the antenna, the reflection coefficient Γm being determined by multiplying the conversion coefficient given as a complex number by a time average of the detection signals in a predetermined period corresponding to one cycle or more time in which heartbeat and respiration waveforms can be measured; and
the current circuit constant of the variable matching circuit.

3. The biosensor device according to claim 1, wherein
the variable matching circuit includes:
a first terminal connected to the signal generator;
second and third terminals connected to the antenna;
a fourth terminal connected to ground;
a first variable capacitance element connected between the first terminal and the second terminal;
a second variable capacitance element connected between the third terminal and the fourth terminal; and
a third variable capacitance element connected between the first terminal and the fourth terminal,
the control circuitry calculates a load impedance Za of the antenna by using
the reflection coefficient Γm of the variable matching circuit and the antenna, the reflection coefficient Γm being determined by multiplying the conversion coefficient by a time average of the detection signal in a predetermined period corresponding to one cycle or more time in which heartbeat and respiration waveforms can be measured on a basis of the detection signal; and a circuit constant of the variable matching circuit, and the control circuitry, by using a condition that the reflection coefficient Γm including impedances of the variable matching circuit and the antenna is zero (50Ω) at the load impedance Za of the antenna, sets an adjustment value for the variable matching circuit so as to satisfy the following formulas, $$C_1 = \cfrac{2}{\omega\left\{X_a - \cfrac{\omega C_2 R_0^2}{1+\omega^2 C_2 (R_0 - R_2)^2}\right\}}$$

-continued $$C_2 = \frac{1}{\omega}\sqrt{\frac{R_0 - (2R_1 + R_a)}{(R_2 - R_0)\{(R_2 - R_0)(R_a + 2R_1) - R_2 R_0\}}}$$

in which a capacitance value of each of the first variable capacitance element and the second variable capacitance element is represented by C1, a value of a series resistance parasitic on each of the first variable capacitance element and the second variable capacitance element is represented by R1, a capacitance value of the third variable capacitance element is represented by C2, a value of a series resistance parasitic on the third variable capacitance element is represented by R2, and a frequency of a signal generated from the signal generator to generate the continuous wave signal is represented by ω.

\* \* \* \* \*